(12) United States Patent
O'Connor

(10) Patent No.: US 11,504,476 B2
(45) Date of Patent: Nov. 22, 2022

(54) CHEMICALLY DRIVEN AUTO-INJECTOR WITH RETRACTION

(71) Applicant: Eli Lilly and Company, Indianapolis, IN (US)

(72) Inventor: Joseph Patrick O'Connor, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 177 days.

(21) Appl. No.: 16/631,510

(22) PCT Filed: Jul. 20, 2018

(86) PCT No.: PCT/US2018/043064
§ 371 (c)(1),
(2) Date: Jan. 16, 2020

(87) PCT Pub. No.: WO2019/023053
PCT Pub. Date: Jan. 31, 2019

(65) Prior Publication Data
US 2020/0197611 A1    Jun. 25, 2020

Related U.S. Application Data

(60) Provisional application No. 62/537,587, filed on Jul. 27, 2017.

(51) Int. Cl.
*A61M 5/20*    (2006.01)
*A61M 5/31*    (2006.01)
(Continued)

(52) U.S. Cl.
CPC ........ *A61M 5/2046* (2013.01); *A61M 5/3148* (2013.01); *A61M 5/31578* (2013.01); *A61M 5/3234* (2013.01); *A61M 2005/206* (2013.01)

(58) Field of Classification Search
CPC ............. A61M 5/2046; A61M 5/3148; A61M 5/31578; A61M 5/3234; A61M 2005/206; A61M 5/2053
See application file for complete search history.

(56) References Cited

U.S. PATENT DOCUMENTS

| | | | |
|---|---|---|---|
| 5,451,210 A * | 9/1995 | Kramer | A61M 5/1723 604/136 |
| 2010/0179473 A1* | 7/2010 | Genosar | A61M 5/14248 604/70 |

(Continued)

FOREIGN PATENT DOCUMENTS

| | | |
|---|---|---|
| WO | 03066138 | 8/2003 |
| WO | 2003068290 | 8/2003 |

(Continued)

OTHER PUBLICATIONS

International Search Report of the International Searching Authority pertaining to International Application No. PCT/US2018/043064; dated Oct. 22, 2018; 7 pages.

(Continued)

*Primary Examiner* — James D Ponton
*Assistant Examiner* — Neeraja Gollamudi
(74) *Attorney, Agent, or Firm* — Jonathan Anderson

(57) ABSTRACT

Automatic injection devices (i.e., auto-injectors) and methods are disclosed that use gas-generating chemical reactions for parenteral delivery of therapeutic fluids. The generated gas may place the auto-injector in a punctured configuration to puncture a patient's skin with a needle, an injected configuration to deliver the therapeutic fluid through the needle and into the puncture site, and/or a retracted configuration to withdraw the needle from the puncture site.

19 Claims, 27 Drawing Sheets

(51) Int. Cl.
*A61M 5/315* (2006.01)
*A61M 5/32* (2006.01)

(56) References Cited

U.S. PATENT DOCUMENTS

2014/0103075 A1  4/2014  Bennison et al.
2016/0015907 A1  1/2016  Edwards et al.

FOREIGN PATENT DOCUMENTS

| WO | 2012103303 | 8/2012 | | |
|---|---|---|---|---|
| WO | 2016065484 | 5/2016 | | |
| WO | 2017004345 | 1/2017 | | |
| WO | WO-2017004345 A1 * | 1/2017 | .......... | A61M 5/3234 |

OTHER PUBLICATIONS

Written Opinion of the International Searching Authority pertaining to International Application No. PCT/US2018/043064; dated Oct. 22, 2018; 12 pages.

* cited by examiner

CHEMICALLY DRIVEN AUTO-INJECTOR WITH RETRACTION

CROSS REFERENCE TO RELATED APPLICATION

This application is a National Stage of International Application No. PCT/US2018/043064, filed Jul. 20, 2018, which claims priority to U.S. Provisional Application Ser. No. 62/537,587, filed Jul. 27, 2017, the disclosures of which are hereby expressly incorporated by reference herein in their entirety.

FIELD OF THE DISCLOSURE

The present disclosure relates to devices and methods for parenteral delivery of therapeutic fluids. More particularly, the present disclosure relates to automatic injection devices (i.e., auto-injectors) and methods that use gas-generating chemical reactions for parenteral delivery of therapeutic fluids.

BACKGROUND OF THE DISCLOSURE

Protein therapeutics is an emerging class of drug therapy that provides treatment for a broad range of diseases, such as autoimmune disorders, cardiovascular diseases, diabetes, and cancer. A common delivery method for some protein therapeutics, such as monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes and injection pens requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics is also challenging because of the high viscosity associated with such therapeutic formulations, and the high forces needed to push such formulations through a parenteral device. Formulations with absolute viscosities above 40-60 centipoise (cP) may be difficult to deliver by conventional spring driven auto-injectors for multiple reasons. Structurally, the footprint of a spring for the amount of pressure delivered is relatively large and fixed to specific shapes, which reduces flexibility of design for delivery devices. Next, auto-injectors are usually made of plastic parts. However, a large amount of energy must be stored in the spring to reliably deliver high-viscosity fluids. If not properly designed, this stored energy may cause damage to the plastic parts due to creep, which is the tendency of the plastic part to permanently deform under stress. An auto-injector typically operates by using the spring to push a needle-containing internal component towards an outer edge of the housing of the syringe. The sound associated with the operation of a spring-based auto-injector may cause patient anxiety, potentially reducing future compliance. The generated pressure versus time profile of such a spring driven auto-injector cannot be readily modified, which prevents users from fine tuning pressure to meet their delivery needs.

It would be desirable to provide processes and devices by which a therapeutic fluid, in particular a high-viscosity fluid, could be self-administered in a reasonable time and with a limited injection space. These processes and devices could be used to deliver high-concentration protein, high-viscosity pharmaceutical formulations, or other therapeutic fluids.

SUMMARY

The present disclosure provides auto-injectors and methods that operate using gas-generating chemical reactions. The generated gas may place the auto-injector in a punctured configuration to puncture a patient's skin with a needle, an injected configuration to deliver a therapeutic fluid through the needle and into the puncture site, and/or a retracted configuration to withdraw the needle from the puncture site.

According to an embodiment of the present disclosure, a device is disclosed for delivering a therapeutic fluid by chemical reaction. The device includes a barrel, an actuator assembly coupled to the barrel and including a first reagent and a second reagent, a syringe coupled to the barrel, the syringe containing the therapeutic fluid and including a needle, and a plunger disposed in the syringe. The device has an actuated configuration in which the first and second reagents react and generate a gas, an injected configuration in which the gas moves the plunger in a first direction to deliver the therapeutic fluid from the syringe, and a retracted configuration in which the gas moves the needle of the syringe in a second direction opposite the first direction.

In one aspect of the device, the device has a punctured configuration in which the gas moves the needle of the syringe in the first direction.

In another aspect of the device, the device further comprises a shield disposed around the syringe, wherein the needle of the syringe extends from the shield in the punctured configuration and is concealed by the shield in the retracted configuration.

In a further aspect of the device, the device has a loaded configuration in which the first and second reagents are separated from each other.

In yet another aspect of the device, the device includes a first piston head and a second piston head, the gas acting on the first piston head in the injected configuration and on the second piston head in the retracted configuration.

In a further aspect of the device, the second piston head has a larger surface area than the first piston head.

In yet another aspect of the device, the second piston head is configured to move axially relative to the first piston head.

In a further aspect of the device, the second piston head is fixed relative to the first piston head.

In yet another aspect of the device, the first piston head is disposed inside the barrel and the second piston head extends outwardly from the barrel.

According to another embodiment of the present disclosure, a device is disclosed for delivering a therapeutic fluid by chemical reaction. The device includes a barrel, an actuator assembly coupled to the barrel and including a first reagent and a second reagent, a syringe coupled to the barrel, the syringe containing the therapeutic fluid and including a needle, a plunger disposed in the syringe, and an air chamber in fluid communication with the plunger. The device has an actuated configuration in which the first and second reagents react and generate a gas in the air chamber, an injected configuration in which the gas in the air chamber moves the plunger in a first direction to deliver the therapeutic fluid from the syringe, and a retracted configuration in which the gas is released from the air chamber through an air passageway to allow movement of the needle of the syringe in a second direction opposite the first direction.

In one aspect of the device, the first piston head is disposed inside the barrel and the second piston head extends outwardly from the barrel.

In another aspect of the device, the device further comprises a piston coupled to the syringe, and a second air chamber in fluid communication with the air passageway and the piston, wherein, in the retracted configuration, the gas travels through the air passageway and into the second air chamber to drive the piston in the second direction.

In a further aspect of the device, the air passageway communicates with the surrounding atmosphere.

In yet another aspect of the device, the device further comprises a spring that is compressed in the injected configuration and released in the retracted configuration.

According to yet another embodiment of the present disclosure, a method for delivering a therapeutic fluid by chemical reaction from a device comprising a barrel having a first chamber, an actuator assembly coupled to the barrel and including a first reagent and a second reagent separated by a barrier, a syringe coupled to the barrel, the syringe containing the therapeutic fluid and including a needle, a plunger disposed in the syringe, and a shield coupled to the barrel and surrounding the syringe is disclosed. The method includes actuating the actuator assembly, at least partially removing the barrier between the first reagent and the second reagent, generating a gas from a reaction of the first reagent and the second reagent, pressurizing the first chamber of the barrel with the generated gas, displacing the syringe, the plunger, and the needle in a first direction via a force created by the generated gas, displacing the plunger within the syringe via the force created by the generated gas, delivering the therapeutic fluid from the needle, releasing the generated gas from the first chamber within the barrel, and displacing the needle and the syringe in a second direction after releasing the generated gas form the first chamber.

In one aspect of the method, the needle of the syringe is positioned within the shield prior to displacement of the syringe, the plunger, and the needle in the first direction via the force created by the generated gas.

In another aspect of the method, the method further comprises exposing the needle of the syringe outside of the shield when the syringe, the plunger, and the needle are displaced in the first direction.

In a further aspect of the method, the second direction is opposite the first direction.

In yet another aspect of the method, the device further includes an air passageway, the step of releasing the generated gas from the first chamber including the generated gas entering the air passageway after the plunger is displaced within the syringe.

In a further aspect of the method, displacement of the syringe and the needle in the second direction occurs after the generated gas enters the air passageway.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
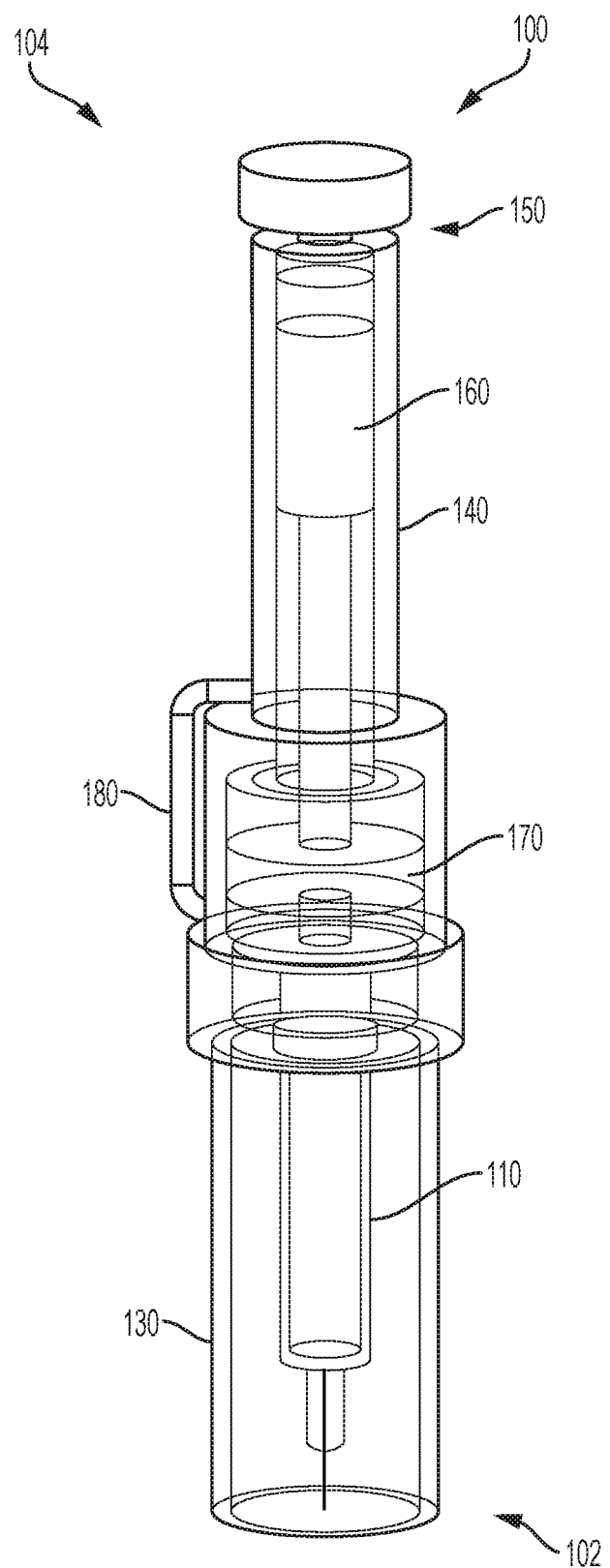
FIG. 1 is a perspective view of a first exemplary delivery device of the present disclosure.

The present disclosure provides auto-injectors and methods that operate using gas-generating chemical reactions. The generated gas may place the auto-injector in a punctured configuration to puncture a patient's skin with a needle, an injected configuration to deliver a therapeutic fluid through the needle and into the puncture site, and/or a retracted configuration to withdraw the needle from the puncture site. Unless specifically noted or clearly implied otherwise, the term "about" refers to a range of values of plus or minus 10%, e.g., about 100 refers to the range 90 to 110.

1. Therapeutic Fluids

The therapeutic fluid to be dispensed from the devices of the present disclosure may take various forms, such as a solution, dispersion, suspension, emulsion, or another suitable fluid form.

The therapeutic fluid may contain a therapeutically useful agent. The therapeutic agent may include insulin, insulin analog such as insulin lispro or insulin glargine, insulin derivative, GLP-1 receptor agonist such as dulaglutide or liraglutide, glucagon, glucagon analog, glucagon derivative, gastric inhibitory polypeptide (GIP), GIP analog, GIP derivative, oxyntomodulin analog, oxyntomodulin derivative, therapeutic antibody and any therapeutic agent that is capable of transport or delivery by the devices of the present disclosure. The therapeutic agent as used in the device may be formulated with one or more excipients.

In certain embodiments, the agent is protein, such as a monoclonal antibody or some other protein which is therapeutically useful. In some embodiments, the protein may have a concentration of from about 75 mg/mL to about 500 mg/mL in the therapeutic fluid. In certain embodiments, the protein may have a concentration of about 150 mg/mL, 200 mg/mL, 250 mg/mL, or more. The therapeutic fluid may further contain a solvent or non-solvent, such as water, perfluoroalkane solvent, safflower oil, or benzyl benzoate.

The therapeutic fluid may be considered a high-viscosity fluid and may have an absolute viscosity of from about 5 cP to about 1000 cP. In certain embodiments, the high-viscosity fluid has an absolute viscosity of at least about 10 cP, 20 cP, 30 cP, 40 cP, 50 cP, 60 cP, or more.

2. Gas-Generating Chemical Reactions

Any suitable chemical reagent or reagents may be used to generate a gas in the devices of the present disclosure. Examples of generated gases include carbon dioxide gas, nitrogen gas, oxygen gas, chlorine gas, etc. Desirably, the generated gas is inert and non-flammable. The amount of gas needed to operate the device may impact the type, amount, and concentration of each reagent used in the device. The reagents may be in dry form (e.g., powdered form, tablet form) and/or in liquid form.

In one exemplary embodiment, a bicarbonate (which may be present in dry form) reacts with an acid (which may be present in liquid form) to produce carbon dioxide gas in the device. Examples of suitable bicarbonates include sodium bicarbonate, potassium bicarbonate, and ammonium bicarbonate. Other ingredients may also be present along with the bicarbonates, such as diatomaceous earth. Examples of suitable acids include acetic acid, citric acid, potassium bitartrate, disodium pyrophosphate, and calcium dihydrogen phosphate. In one particular example, the bicarbonate is potassium bicarbonate and the acid is aqueous citric acid, which may react to produce carbon dioxide gas and a liquid mixture of water and dissolved potassium citrate.

Other reactions may be used to drive the devices of the present disclosure. In one example, a metal carbonate, such as copper carbonate or calcium carbonate, is thermally decomposed to produce carbon dioxide gas and the corresponding metal oxide in the device. In another example, 2,2'-azobisisobutyronitrile (AIBN) is heated to produce nitrogen gas in the device. In yet another example, enzymes (e.g. yeast) are reacted with sugar to produce carbon dioxide gas in the device. Some substances readily sublime, going from solid to gas. Such substances include but are not limited to naphthalene and iodine. In still yet another example, hydrogen peroxide is decomposed with catalysts such as enzymes (e.g. catalase) or manganese dioxide to produce oxygen gas in the device. In still yet another example, silver chloride is decomposed through exposure to light to generate a gas in the device.

Suitable reagents, chemical formulations, and reactions used to operate the devices of the present disclosure are further described in the following references, the disclosures of which are expressly incorporated herein by reference in their entirety: U.S. Pat. No. 9,321,581, filed Oct. 15, 2013, and titled "Process and Device for Delivery of Fluid by Chemical Reaction"; U.S. Pat. No. 9,795,740 (U.S. application Ser. No. 14/434,586), filed Oct. 15, 2013, and titled "Chemical Engines and Methods for Their Use, Especially in the Injection of Highly Viscous Fluids"; and International Patent Application No. PCT/US2018/017547, filed Feb. 9, 2018, and titled "Processes and Devices for Delivery of Fluid by Chemical Reaction".

3. First Embodiment

Figure 2:
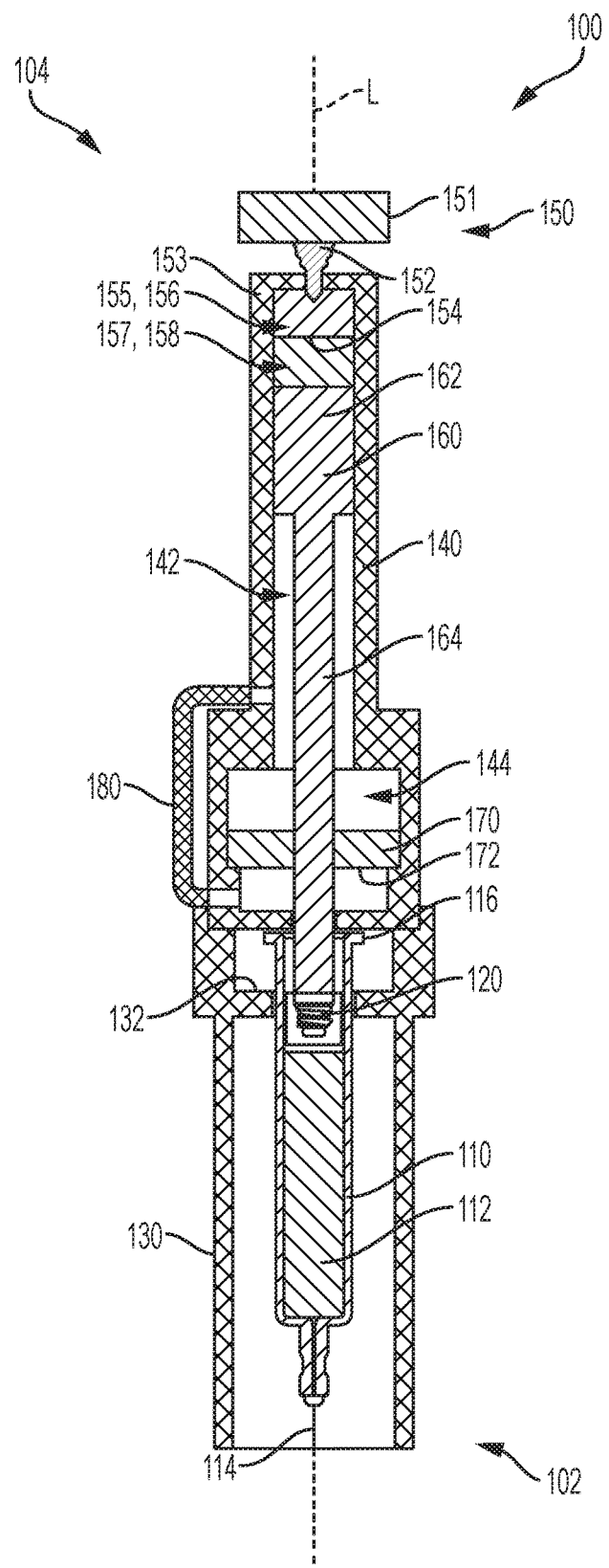
FIG. 2 is a cross-sectional view of the first delivery device of FIG. 1, shown in a loaded configuration.

FIGS. 1 and 2 show a first exemplary delivery device 100 of the present disclosure. The illustrative device 100 is an elongate structure that extends along longitudinal axis L from a first, distal end 102 (illustratively, a lower end) to a second, proximal end 104 (illustratively, an upper end). Advantageously, device 100 may have a compact construction and a relatively short length. Distal end 102 of device 100 includes a syringe 110, a plunger 120, and a shield 130. Proximal end 104 of device 100 includes barrel 140, an actuator assembly 150, a first piston 160, a second piston 170, and an airway 180. Each component of device 100 is described further below with continued reference to FIGS. 1 and 2.

The illustrative syringe 110 contains a therapeutic fluid 112, as discussed above. At distal end 102, syringe 110 includes a needle 114 configured to puncture a patient's skin. At its other end, syringe 110 includes a rim 116 configured to interact with shield 130. In use, syringe 110 is configured for longitudinal movement with first piston 160 relative to shield 130 and barrel 140.

The illustrative plunger 120 is disposed within syringe 110 and coupled to the distal end of first piston 160. In use, plunger 120 is configured for longitudinal movement with first piston 160.

The illustrative shield 130 is disposed around syringe 110 and is coupled (e.g., threaded, welded) to barrel 140. It is also within the scope of the present disclosure for shield 130 to be integrally formed with barrel 140. Shield 130 includes an interior shoulder 132 configured to contact rim 116 of syringe 110 to limit distal movement of syringe 110.

The illustrative barrel 140 is substantially cylindrical in shape, although this shape may vary. Barrel 140 includes an upper chamber 142 having a relatively small internal diameter and a lower chamber 144 having a relatively large internal diameter.

The illustrative actuator assembly 150 includes a button 151 having a sharp distal tip 152. The illustrative actuator assembly 150 also includes a housing 153 having an interior barrier 154 (e.g., film). In the illustrated embodiment of FIG. 2, housing 153 of actuator assembly 150 is integrally formed with barrel 140, but it is also within the scope of the present disclosure for housing 153 of actuator assembly 150 and barrel 140 to be separate components. In the configuration shown in FIG. 2, interior barrier 154 divides housing 153 into a first actuation chamber 155 that contains a first reagent 156 (e.g., aqueous citric acid) and a second reaction chamber 157 that contains a second reagent 158 (e.g., potassium bicarbonate).

The illustrative first piston 160 includes a head 162 disposed in upper chamber 142 of barrel 140 and a shaft 164 disposed in syringe 110. As indicated above, longitudinal movement of the first piston 160 may be transferred to plunger 120.

The illustrative second piston 170 includes a head 172 disposed in lower chamber 144 of barrel 140. As shown in FIG. 2, second piston 170 surrounds shaft 164 of first piston 160 beneath head 162 of first piston 160. In use, second piston 170 is configured to slide axially across shaft 164 of first piston 160. The surface area of head 172 of second piston 170 may exceed the surface area of head 162 of first piston 160.

The illustrative airway 180 connects upper chamber 142 of barrel 140 with lower chamber 144 of barrel 140. Although the illustrative airway 180 is an external tube that extends outside of barrel 140, it is within the scope of the present disclosure that airway 180 may be incorporated into barrel 140. In use, when airway 180 is open, airway 180 is configured to direct gas from upper chamber 142 of barrel 140 into lower chamber 144 of barrel 140.

Referring next to FIGS. 2-6, an exemplary method is shown and described for operating device 100.

In FIG. 2, device 100 is shown in a loaded configuration. It is within the scope of the present disclosure for device 100 to be locked in this loaded configuration until device 100 is ready for use. At distal end 102 of device 100, syringe 110 and needle 114 are withdrawn into and concealed by shield 130. At proximal end 104 of device 100, interior barrier 154 of actuator assembly 150 separates first reagent 156 (e.g., aqueous citric acid) in first actuation chamber 155 from second reagent 158 (e.g., potassium bicarbonate) in second reaction chamber 157.

Figure 3:
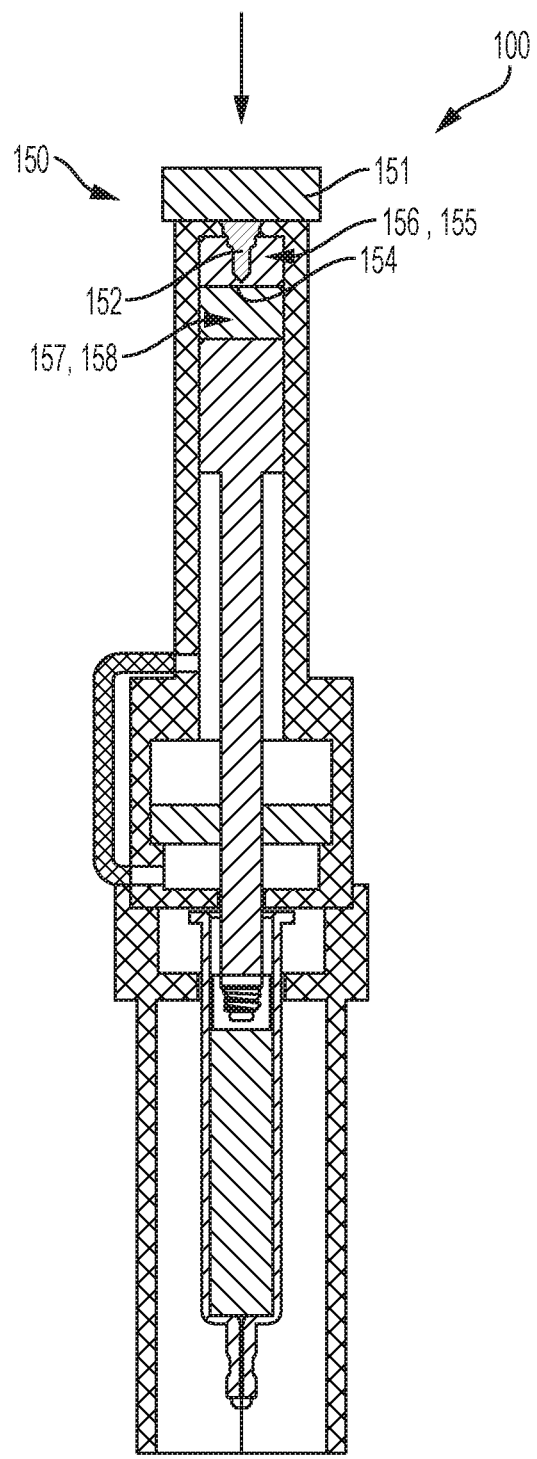
FIG. 3 is another cross-sectional view of the first delivery device of FIG. 1, shown in an actuated configuration.

In FIG. 3, device 100 is shown in an actuated configuration. Button 151 of actuator assembly 150 has been pressed to pierce interior barrier 154 with tip 152. As a result, interior barrier 154 between first reaction chamber 155 and second reaction chamber 157 is at least partially removed such that first reagent 156 (e.g., aqueous citric acid) in first actuation chamber 155 is exposed to second reagent 158 (e.g., potassium bicarbonate) in second reaction chamber 157.

Additional details regarding actuator assembly 150 and other suitable actuator assemblies are described in the above-incorporated U.S. Pat. Nos. 9,321,581; 9,795,740; and International Application No. PCT/US2018/017547. For example, in one alternative embodiment disclosed in the above-incorporated PCT/US2018/017547, the actuator assembly includes a piston (not shown) and a spring (not shown). In the loaded configuration, the piston compresses the spring and creates a sealed interface between the first and second chambers 155, 157. In the actuated configuration, the spring releases and moves the piston to break the sealed interface between the first and second chambers in 155, 157.

Figure 4:
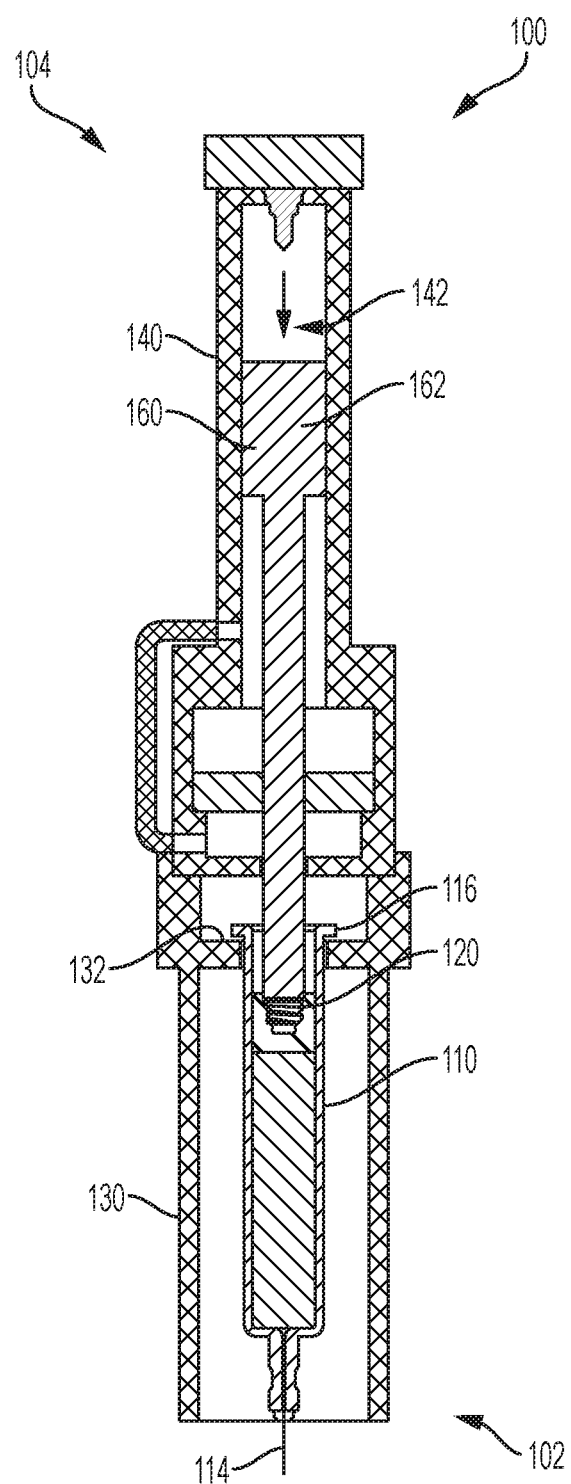
FIG. 4 is another cross-sectional view of the first delivery device of FIG. 1, shown in a punctured configuration.

In FIG. 4, device 100 is shown in a punctured configuration. At proximal end 104 of device 100, first and second reagents 156, 158 react and generate gas. The gas pressurizes upper chamber 142 of barrel 140 and applies force to head 162 of first piston 160, which causes first piston 160 to move distally through barrel 140. Due to frictional forces between syringe 110 and plunger 120, the initial distal movement of first piston 160 causes distal movement of syringe 110, until rim 116 of syringe 110 abuts interior shoulder 132 of shield 130. At distal end 102 of device 100, needle 114 protrudes from shield 130 to puncture the patient's skin.

Figure 5:
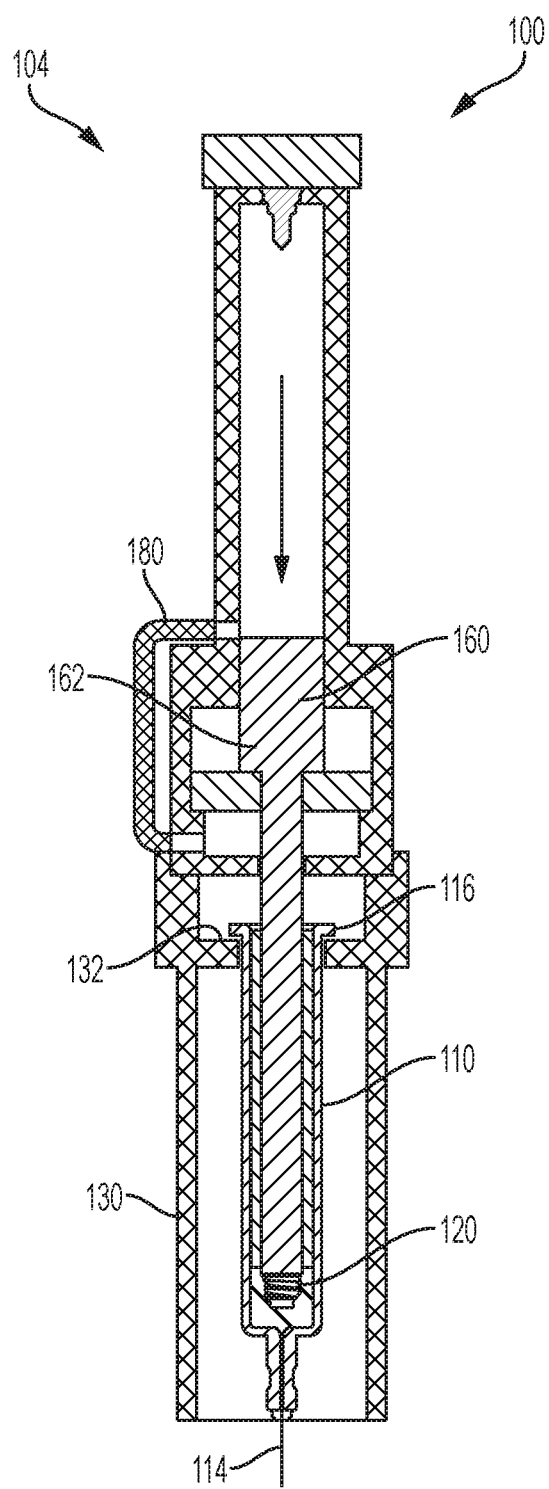
FIG. 5 is another cross-sectional view of the first delivery device of FIG. 1, shown in an injected configuration.

In FIG. 5, device 100 is shown in an injected configuration. At proximal end 104 of device 100, first and second reagents 156, 158 continue to react and generate gas. With rim 116 of syringe 110 abutting interior shoulder 132 of shield 130, the continued distal movement of first piston 160 overcomes frictional forces between plunger 120 and syringe 110 and causes distal movement of plunger 120 through syringe 110 to deliver therapeutic fluid 112 from syringe 110, through needle 114, and into the puncture site. When first piston 160 reaches the end of its distal stroke, as shown in FIG. 5, head 162 of first piston 160 moves past and exposes airway 180.

Figure 6:
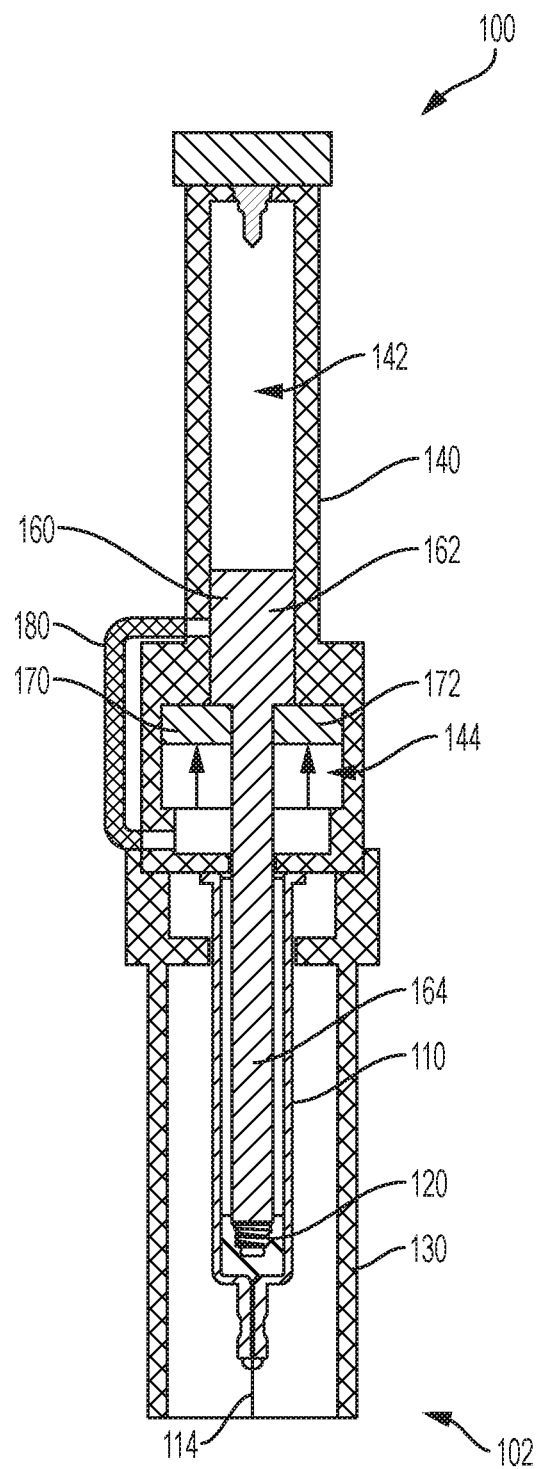
FIG. 6 is another cross-sectional view of the first delivery device of FIG. 1, shown in a retracted configuration.

In FIG. 6, device 100 is shown in a retracted configuration. To reach this configuration, the gas from upper chamber 142 of barrel 140 is released from upper chamber 142 and travels through the exposed airway 180 and into lower chamber 144 of barrel 140. Eventually, because the surface area of head 172 of second piston 170 exceeds the surface area of head 162 of first piston 160, the proximal force on second piston 170 may overcome the distal force on first piston 160, even when the pressure in lower chamber 144 is equal to or less than the pressure in upper chamber 142. When the proximal force eventually exceeds the distal force after a certain delay time, second piston 170 moves proximally through lower chamber 144 of barrel 140 toward first piston 160. The proximal movement of second piston 170, including the delay time before movement, may be controlled by adjusting the size and shape of first piston 160, the size and shape of second piston 170, and the size of airway 180, for example. When second piston 170 reaches head 162 of first piston 160, the continued proximal movement of second piston 170 causes proximal movement of first piston 160. Due to frictional forces between syringe 110 and plunger 120, the proximal movement of first piston 160 causes proximal movement of syringe 110. At distal end 102 of device 100, needle 114 withdraws from the puncture site and retracts into shield 130. Needle 114 may have the same position in the retracted configuration of FIG. 6 as the loaded configuration of FIG. 2. First piston 160 and/or second piston 170 may be captured at the end of the proximal stroke, such as using an expanding C-ring, to maintain needle 114 in the retracted configuration.

4. Second Embodiment

FIGS. 7-11 show a second exemplary delivery device 200 of the present disclosure. The illustrative device 200 is similar to delivery device 100 described above, except that first piston 260 and second piston 270 are coupled or fixed together or integral to form a dual-piston body 265 including both first piston 260 and second piston 270. Piston body 265 is positioned within proximal end 204 of device 200. In order for the pistons 260, 270 to be integrally formed, device 200 is slightly elongated along longitudinal axis L compared to device 100. Similar to device 100, distal end 202 of device 200 includes a syringe 210, a plunger 220, and a shield 230, and proximal end 204 of device 200 includes barrel 240, an actuator assembly 250, and an airway 280. Each component of device 200 is described further below with continued reference to FIGS. 7-11.

The illustrative syringe 210 contains a therapeutic fluid 212, as discussed above. At distal end 202, syringe 210 includes a needle 214 configured to puncture a patient's skin. At its other end, syringe 210 includes a rim 216 configured to interact with shield 230. In use, syringe 210 is configured for longitudinal movement with piston body 265 relative to shield 230 and barrel 240.

The illustrative plunger 220 is disposed within syringe 210 and coupled to the distal end of piston body 265. In use, plunger 220 is configured for longitudinal movement with piston body 265.

The illustrative shield 230 is disposed around syringe 210 and is coupled (e.g., threaded, welded) to barrel 240. It is also within the scope of the present disclosure for shield 230 to be integrally formed with barrel 240. Shield 230 includes an interior shoulder 232 configured to contact rim 216 of syringe 210 to limit distal movement of syringe 210.

The illustrative barrel 240 is substantially cylindrical in shape, although this shape may vary. Barrel 240 includes an upper chamber 242 having a relatively small internal diameter and a lower chamber 244 having a relatively large internal diameter.

The illustrative actuator assembly 250 includes a button 251 having a sharp distal tip 252. The illustrative actuator assembly 250 also includes a housing 253 having an interior barrier 254 (e.g., film). In the illustrated embodiment of FIG. 7, housing 253 of actuator assembly 250 is integrally formed with barrel 240, but it is also within the scope of the present disclosure for housing 253 of actuator assembly 250 and barrel 240 to be separate components. In the configuration shown in FIG. 7, interior barrier 254 divides housing 253 into a first actuation chamber 255 that contains a first reagent 256 (e.g., aqueous citric acid) and a second reaction chamber 257 that contains a second reagent 258 (e.g., potassium bicarbonate).

The illustrative piston body 265 includes first piston 260 having a head 262 disposed in upper chamber 242 of barrel 240, a second piston 270 having a head 272 disposed in lower chamber 244 of barrel 240, and a shaft 264 coupling first and second piston 260 and 270. The upper end of shaft 264 is coupled beneath head 262 of first piston 260, and the lower end of shaft 246 extends past second piston 270 and into syringe 210. In use, second piston 270 and first piston 260 are configured to slide longitudinally simultaneously.

The surface area of head 272 of second piston 270 may exceed the surface area of head 262 of first piston 260. As indicated above, longitudinal movement of the piston body 265 may be transferred to plunger 220.

The illustrative airway 280 connects upper chamber 242 of barrel 240 with lower chamber 244 of barrel 240. Although the illustrative airway 280 is an external tube that extends outside of barrel 240, it is within the scope of the present disclosure that airway 280 may be incorporated into barrel 240. In use, when airway 280 is open, airway 280 is configured to direct gas from upper chamber 242 of barrel 240 into lower chamber 244 of barrel 240. Due to the extended length of device 200, airway 280 may also be extended in length to properly couple upper chamber 242 and lower chamber 244.

Referring next to FIGS. 7-11, an exemplary method is shown and described for operating device 200.

Figure 7:
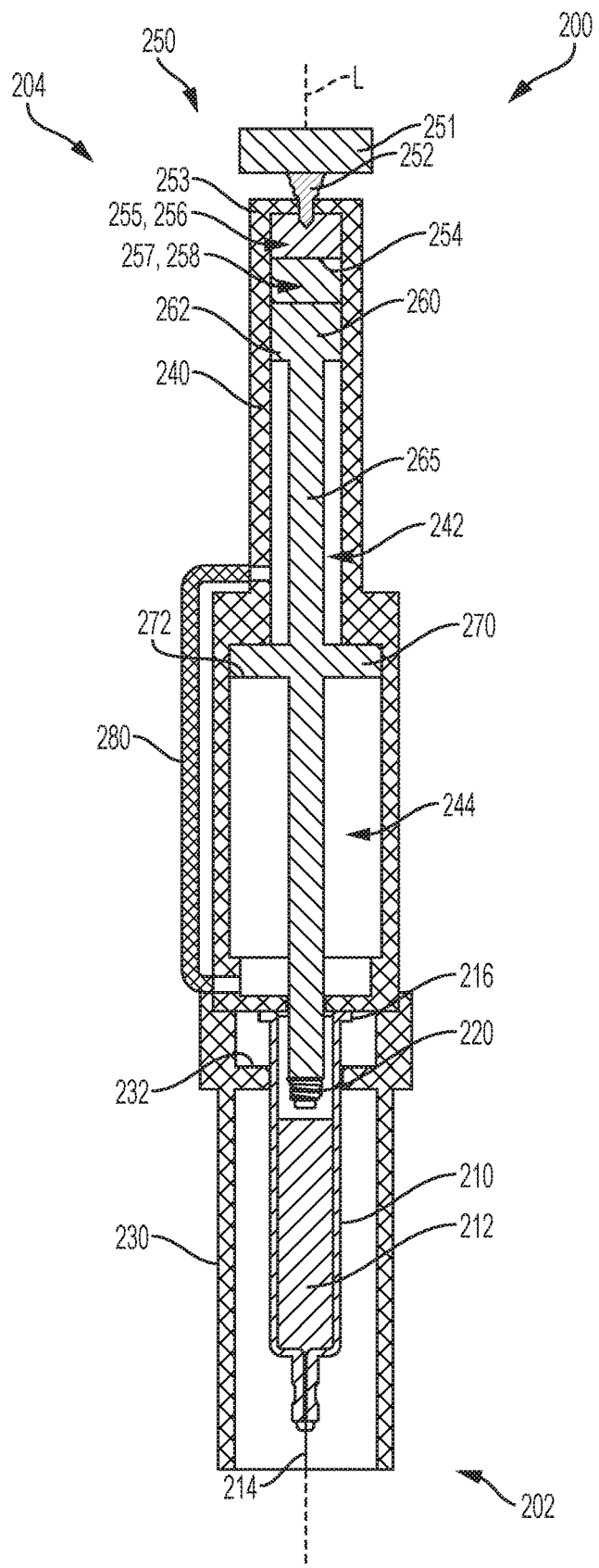
FIG. 7 is a cross-sectional view of a second exemplary delivery device of the present disclosure, shown in a loaded configuration.

In FIG. 7, device 200 is shown in a loaded configuration. It is within the scope of the present disclosure for device 200 to be locked in this loaded configuration until device 200 is ready for use. At distal end 202 of device 200, syringe 210 and needle 214 are withdrawn into and concealed by shield 230. At proximal end 204 of device 200, interior barrier 254 of actuator assembly 250 separates first reagent 256 (e.g., aqueous citric acid) in first actuation chamber 255 from second reagent 258 (e.g., potassium bicarbonate) in second reaction chamber 257.

Figure 8:
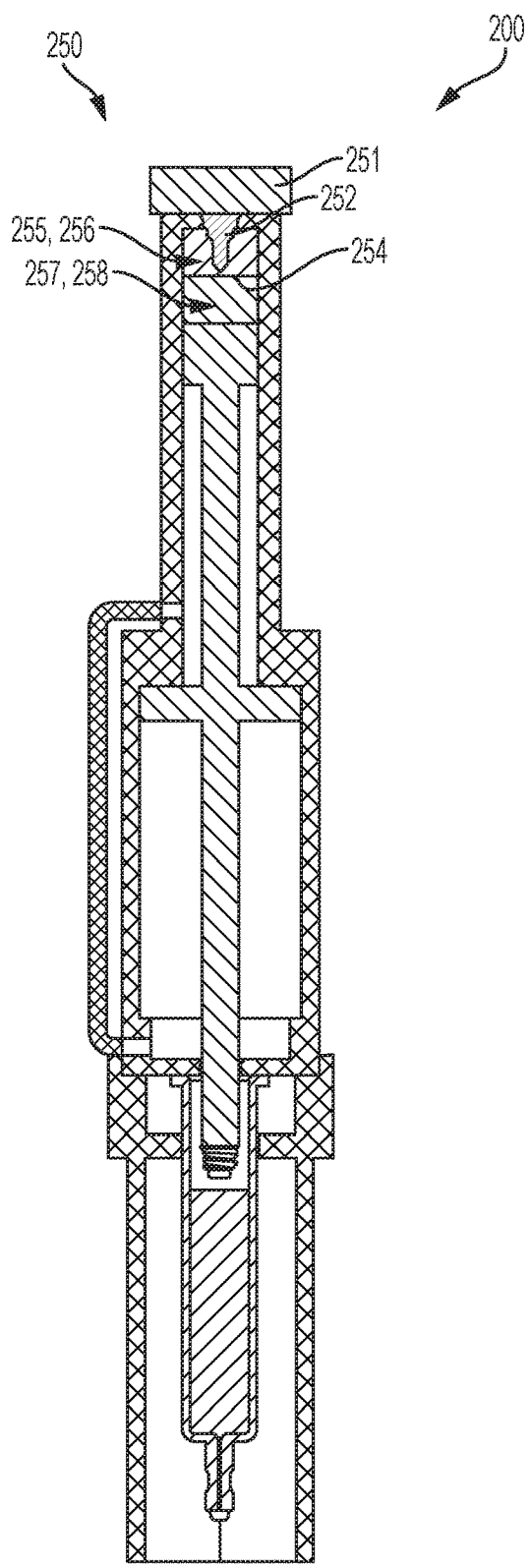
FIG. 8 is another cross-sectional view of the second delivery device of FIG. 7, shown in an actuated configuration.

In FIG. 8, device 200 is shown in an actuated configuration. Button 251 of actuator assembly 250 has been pressed to pierce interior barrier 254 with tip 252. As a result, interior barrier 254 between first reaction chamber 255 and second reaction chamber 257 is at least partially removed such that first reagent 256 (e.g., aqueous citric acid) in first actuation chamber 255 is exposed to second reagent 258 (e.g., potassium bicarbonate) in second reaction chamber 257.

Additional details regarding actuator assembly 250 and other suitable actuator assemblies are described in the above-incorporated U.S. Pat. Nos. 9,321,581; 9,795,740; and International Application No. PCT/US2018/017547, as discussed above.

Figure 9:
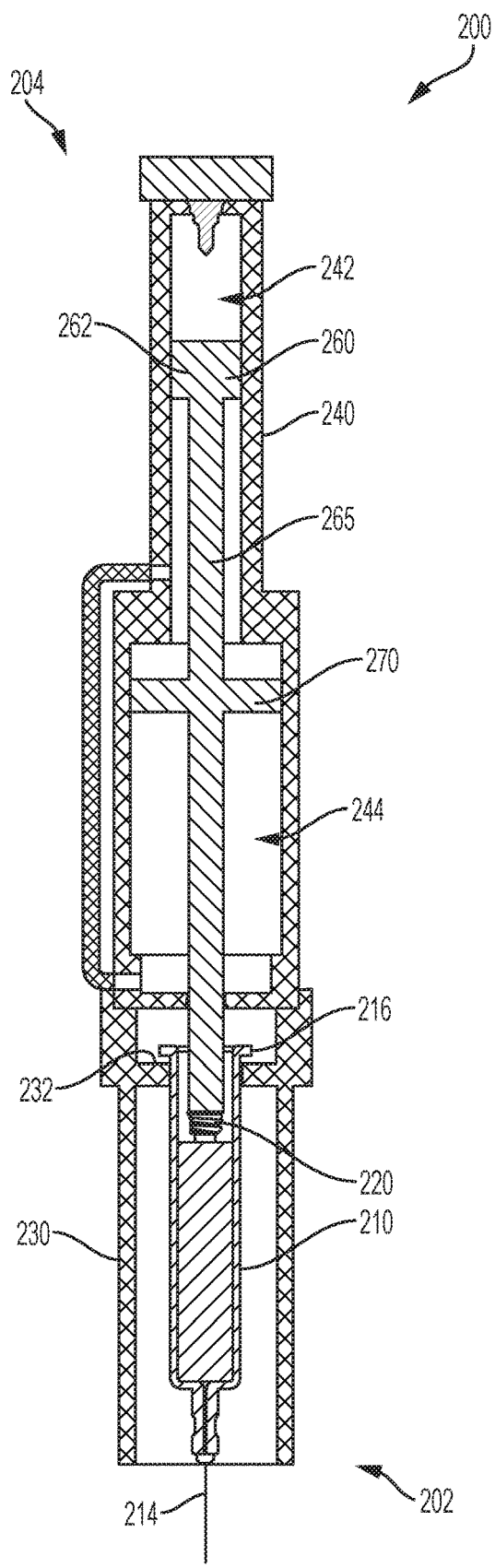
FIG. 9 is another cross-sectional view of the second delivery device of FIG. 7, shown in a punctured configuration.

In FIG. 9, device 200 is shown in a punctured configuration. At proximal end 204 of device 200, first and second reagents 256, 258 react and generate gas. The gas pressurizes upper chamber 242 of barrel 240 and applies force to head 262 of first piston 260 of piston body 265, which causes piston body 265 to move distally through barrel 240, and thus first and second pistons 260 and 270 to move distally through barrel 240 and lower chamber 244, respectively. Due to frictional forces between syringe 210 and plunger 220, the initial distal movement of piston body 265 causes distal movement of syringe 210, until rim 216 of syringe 210 abuts interior shoulder 232 of shield 230. At distal end 202 of device 200, needle 214 protrudes from shield 230 to puncture the patient's skin.

Figure 10:
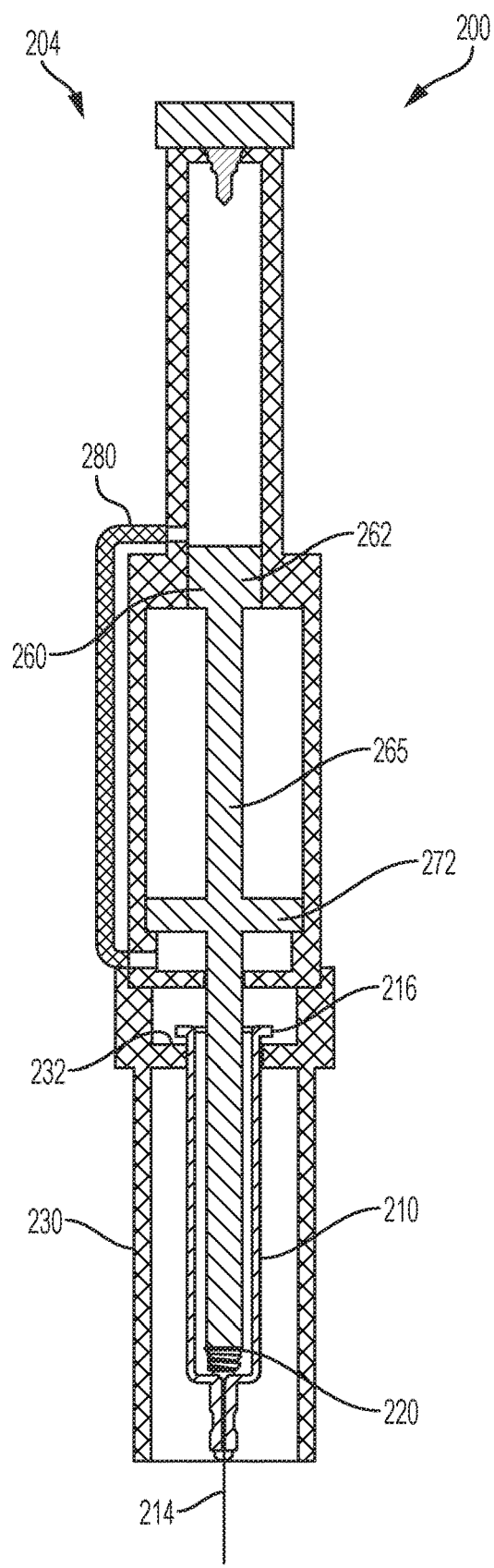
FIG. 10 is another cross-sectional view of the second delivery device of FIG. 7, shown in an injected configuration.

In FIG. 10, device 200 is shown in an injected configuration. At proximal end 204 of device 200, first and second reagents 256, 258 continue to react and generate gas. With rim 216 of syringe 210 abutting interior shoulder 232 of shield 230, the continued distal movement of piston body 265 overcomes frictional forces between plunger 220 and syringe 210 and causes distal movement of plunger 220 through syringe 210 to deliver therapeutic fluid 212 from syringe 210, through needle 214, and into the puncture site. When piston body 265 reaches the end of its distal stroke, as shown in FIG. 10, head 262 of first piston 260 moves past and exposes airway 280.

Figure 11:
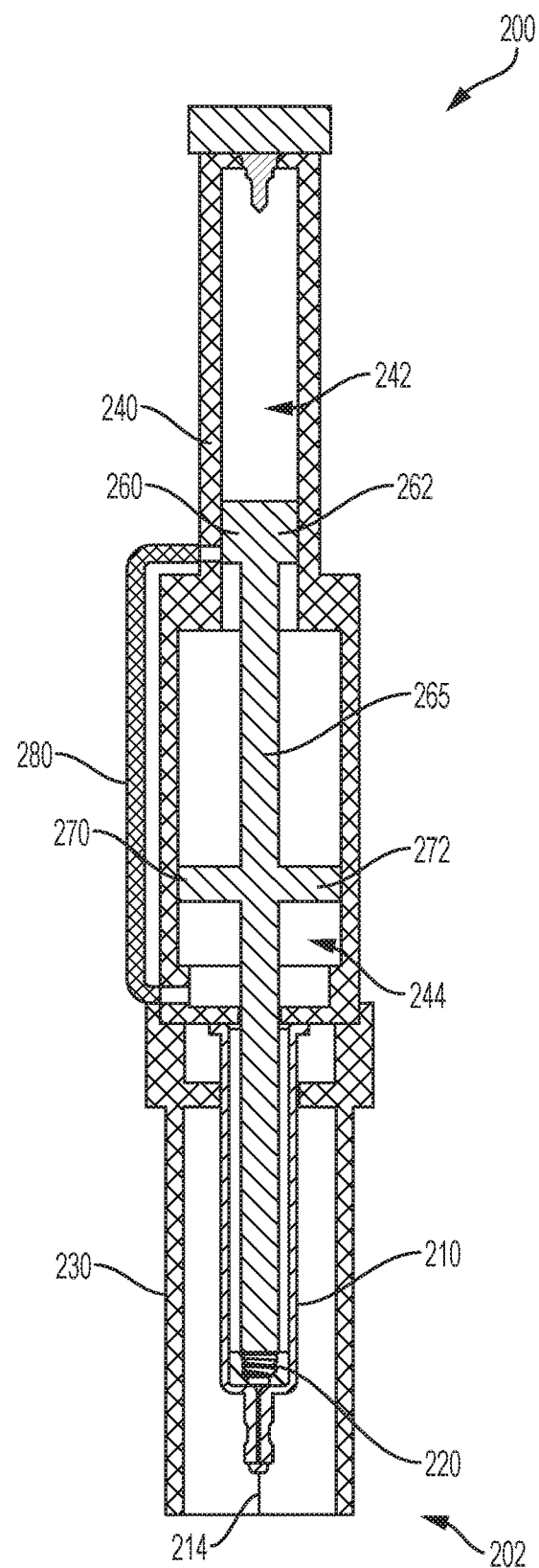
FIG. 11 is another cross-sectional view of the second delivery device of FIG. 7, shown in a retracted configuration.
Figure 12:
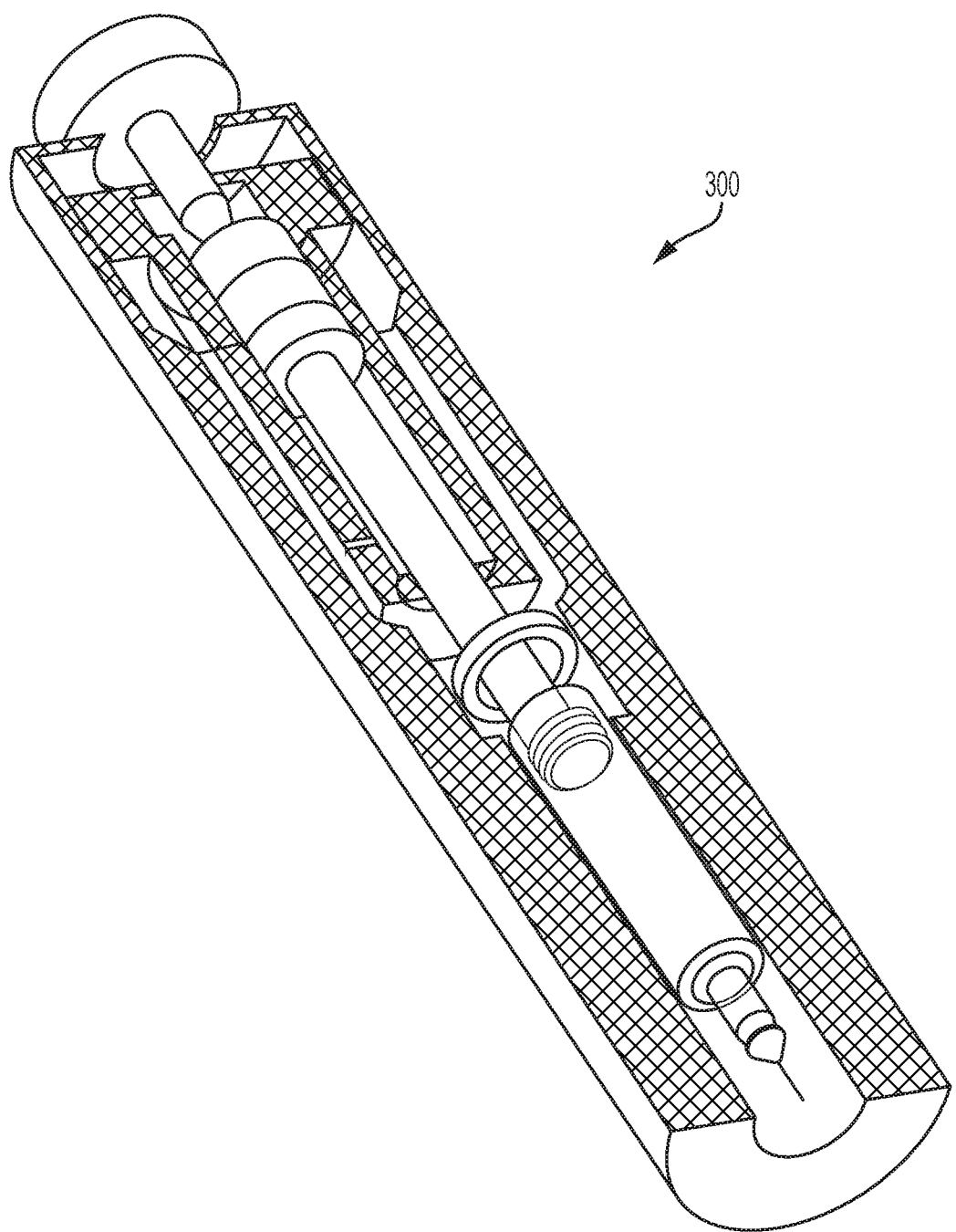
FIG. 12 is a perspective cut-away view of a third exemplary delivery device of the present disclosure.

In FIG. 11, device 200 is shown in a retracted configuration. To reach this configuration, the gas from upper chamber 242 of barrel 240 is released from upper chamber 242 and travels through the exposed airway 280 and into lower chamber 244 of barrel 240. Eventually, because the surface area of head 272 of second piston 270 exceeds the surface area of head 262 of first piston 260, the proximal force on second piston 270 may overcome the distal force on first piston 260, even when the pressure in lower chamber 244 is equal to or less than the pressure in upper chamber 242. When the proximal force eventually exceeds the distal force after a certain delay time, piston body 265 moves proximally through barrel 240. The proximal movement of piston body 265, including the delay time before movement, may be controlled by adjusting the size and shape of first piston 260, the size and shape of second piston 270, and the size of airway 280, for example. Due to frictional forces between syringe 210 and plunger 220, the proximal movement of piston body 265 causes proximal movement of syringe 210. At distal end 202 of device 200, needle 214 withdraws from the puncture site and retracts into shield 230. Needle 214 may have the same position in the retracted configuration of FIG. 11 as the loaded configuration of FIG. 7. First piston 260 and/or second piston 270 may be captured at the end of the proximal stroke to maintain needle 214 in the retracted configuration.

5. Third Embodiment

FIGS. 12-18 show a second exemplary delivery device 300 of the present disclosure. The illustrative device 300 is generally similar to delivery devices 100 and 200 described above, except that device 300 has been configured such that airway 380 is positioned internally within device 300 between an outer housing 335 of device 300 and barrel 340 to act on barrel 340. Distal end 302 of device 300 includes a syringe 310, a plunger 320, and a shield 330, and proximal end 304 of device 300 includes barrel 340, an actuator assembly 350, a piston 360, and airway 380. Each component of device 300 is described further below with continued reference to FIGS. 12-18.

The illustrative syringe 310 contains a therapeutic fluid 312, as discussed above. At distal end 302, syringe 310 includes a needle 314 configured to puncture a patient's skin. At its other end, syringe 310 includes a rim 316 configured to interact with shield 330. In use, syringe 310 is configured for longitudinal movement with piston 360 relative to shield 330 and barrel 340.

The illustrative plunger 320 is disposed within syringe 310 and coupled to the distal end of piston 360. In use, plunger 320 is configured for longitudinal movement with piston 360.

The illustrative shield 330 is disposed around syringe 310 and is integrally formed with outer housing 335. It is also within the scope of the present disclosure for shield 330 to be coupled (e.g., threaded, welded) to outer housing 335. Shield 330 includes an interior shoulder 332 configured to contact rim 316 of syringe 310 to limit distal movement of syringe 310.

The illustrative barrel 340 has an upper piston head 341 (FIG. 16) and is substantially T-shaped, although this shape may vary. Barrel 340 is configured for longitudinal movement relative to outer housing 335. Barrel 340 also includes an inner chamber 342 having a relatively small internal diameter.

The illustrative actuator assembly 350 includes a button 351 having a sharp distal tip 352. The illustrative actuator assembly 350 also includes a housing 353 having an interior barrier 354 (e.g., film). In the illustrated embodiment of FIG. 13, housing 353 of actuator assembly 350 is integrally formed with barrel 340, but it is also within the scope of the present disclosure for housing 353 of actuator assembly 350 and barrel 340 to be separate components. In the configuration shown in FIG. 13, interior barrier 354 divides housing 353 into a first actuation chamber 355 that contains a first reagent 356 (e.g., aqueous citric acid) and a second reaction chamber 357 that contains a second reagent 358 (e.g., potassium bicarbonate).

The illustrative piston 360 has a head 362 disposed in inner chamber 342 of barrel 340 and a shaft 365 that extends downward from head 362 and into syringe 310. As indicated above, longitudinal movement of the piston 360 may be transferred to plunger 320.

The illustrative airway 380 connects inner chamber 342 of barrel 340 with outer chamber 346 of barrel 340 defined by outer housing 335. Although the illustrative airway 380 is an internal passage that extends within of outer housing 335, it is within the scope of the present disclosure that airway 380 may external to outer housing 335. In use, when airway 380 is open, airway 380 is configured to release gas from inner chamber 342 of barrel 340 and direct the gas into outer chamber 346 of barrel 340 defined by outer housing 335.

Referring next to FIGS. 13-18, an exemplary method is shown and described for operating device 300.

Figure 13:
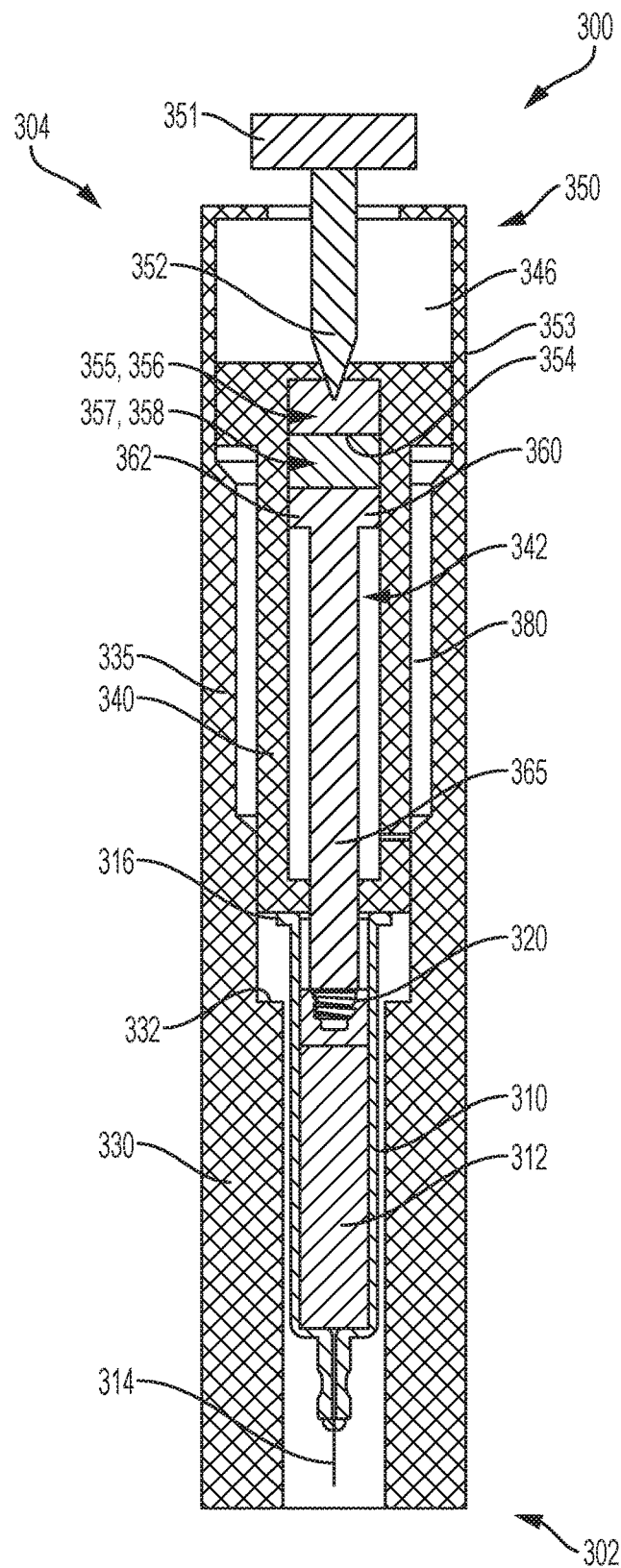
FIG. 13 is a cross-sectional view of the third delivery device of FIG. 12, shown in a loaded configuration.

In FIG. 13, device 300 is shown in a loaded configuration. It is within the scope of the present disclosure for device 300 to be locked in this loaded configuration until device 300 is ready for use. At distal end 302 of device 300, syringe 310 and needle 314 are withdrawn into and concealed by shield 330. At proximal end 304 of device 300, interior barrier 354 of actuator assembly 350 separates first reagent 356 (e.g., aqueous citric acid) in first actuation chamber 355 from second reagent 358 (e.g., potassium bicarbonate) in second reaction chamber 357.

Figure 14:
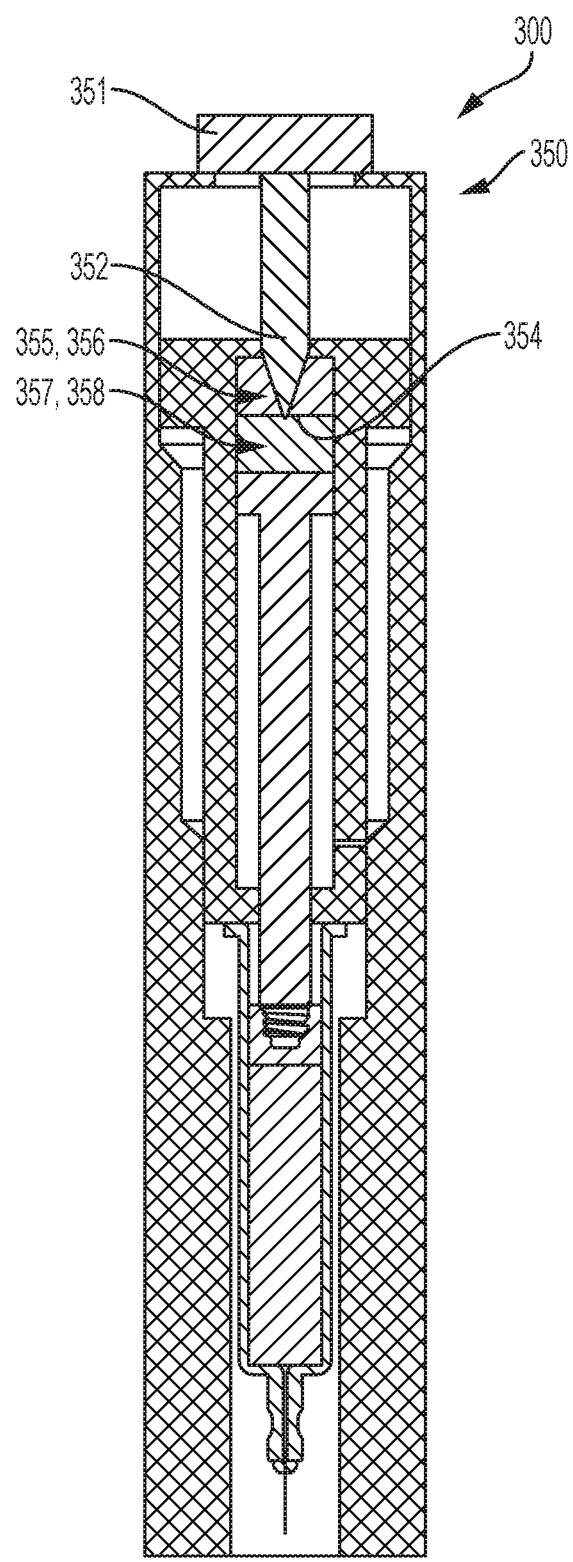
FIG. 14 is another cross-sectional view of the third delivery device of FIG. 12, shown in an actuated configuration.

In FIG. 14, device 300 is shown in an actuated configuration. Button 351 of actuator assembly 350 has been pressed to pierce interior barrier 354 with tip 352. As a result, interior barrier 354 between first reaction chamber 355 and second reaction chamber 357 is at least partially removed such that first reagent 356 (e.g., aqueous citric acid) in first actuation chamber 355 is exposed to second reagent 358 (e.g., potassium bicarbonate) in second reaction chamber 357.

Additional details regarding actuator assembly 350 and other suitable actuator assemblies are described in the above-incorporated U.S. Pat. Nos. 9,321,581; 9,795,740; and International Application No. PCT/US2018/017547, as discussed above.

Figure 15:
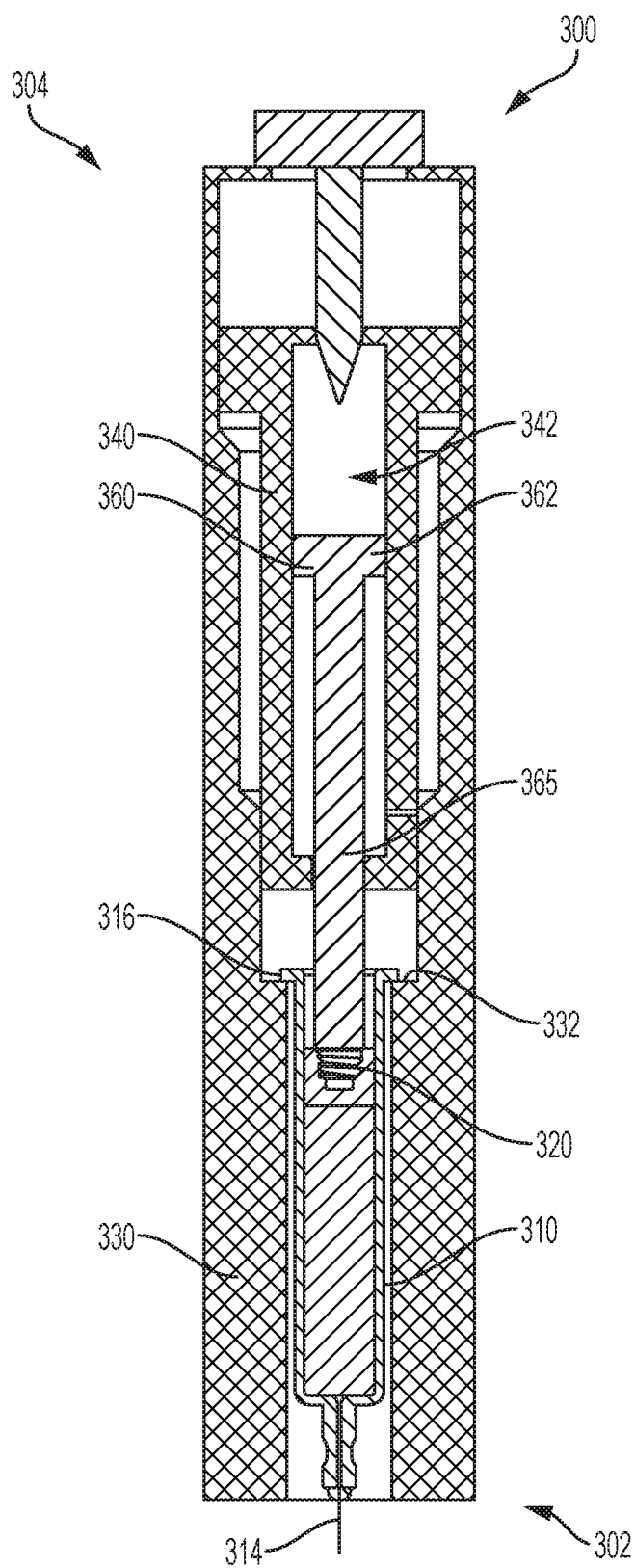
FIG. 15 is another cross-sectional view of the third delivery device of FIG. 12, shown in a punctured configuration.

In FIG. 15, device 300 is shown in a punctured configuration. At proximal end 304 of device 300, first and second reagents 356, 358 react and generate gas. The gas pressurizes inner chamber 342 of barrel 340 and applies force to head 362 of piston 360, which causes piston 360 to move distally through barrel 340. Due to frictional forces between syringe 310 and plunger 320, the initial distal movement of piston 360 causes distal movement of syringe 310, until rim 316 of syringe 310 abuts interior shoulder 332 of shield 330. At distal end 302 of device 300, needle 314 protrudes from shield 330 to puncture the patient's skin.

Figure 16:
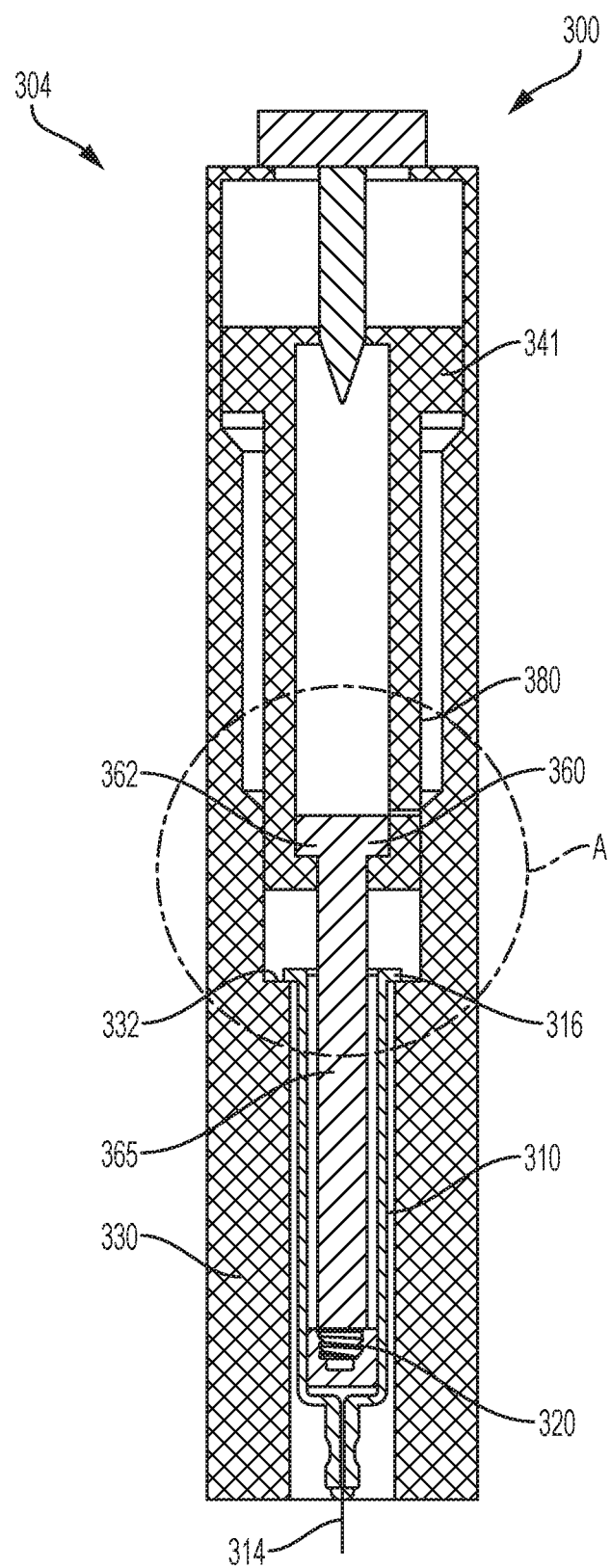
FIG. 16 is another cross-sectional view of the third delivery device of FIG. 12, shown in an injected configuration.
Figure 17:
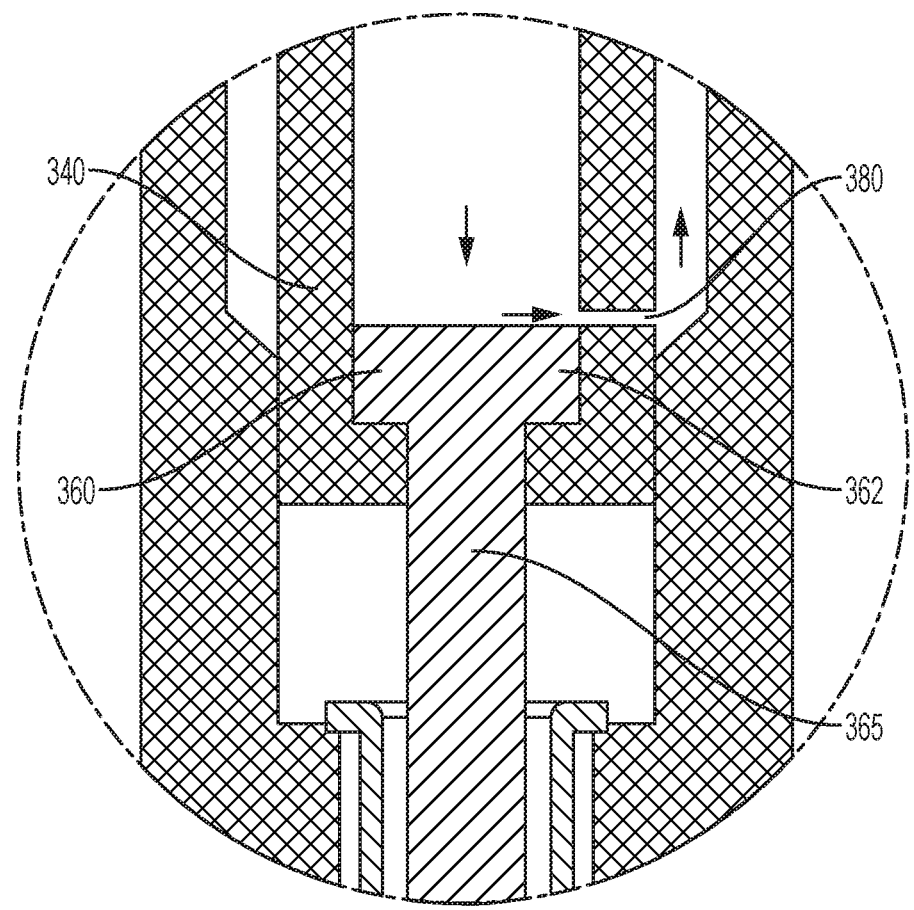
FIG. 17 is a detailed view of section A of the third delivery device of FIG. 16.

In FIG. 16, device 300 is shown in an injected configuration. At proximal end 304 of device 300, first and second reagents 356, 358 continue to react and generate gas. With rim 316 of syringe 310 abutting interior shoulder 332 of shield 330, the continued distal movement of piston 360 overcomes frictional forces between plunger 320 and syringe 310 and causes distal movement of plunger 320 through syringe 310 to deliver therapeutic fluid 312 from syringe 310, through needle 314, and into the puncture site. When piston 360 reaches the end of its distal stroke, as shown in FIG. 16, head 362 of first piston 360 moves past and exposes airway 380, as shown in detail in FIG. 17.

Figure 18:
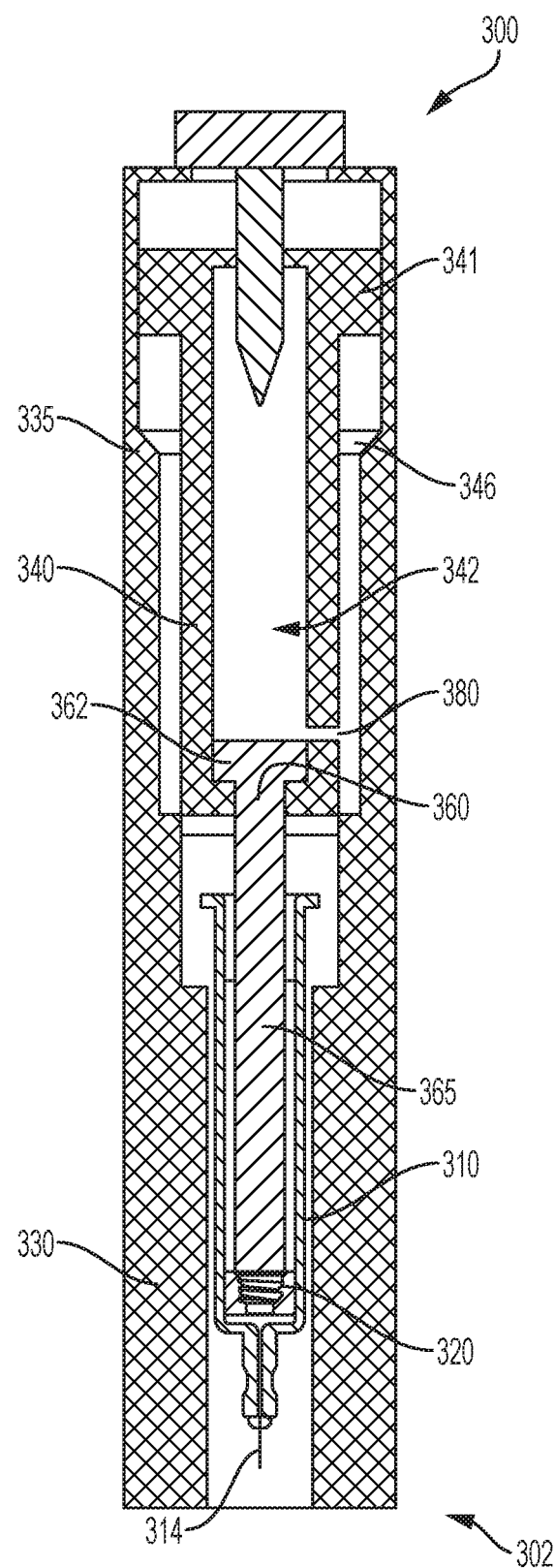
FIG. 18 is another cross-sectional view of the third delivery device of FIG. 12, shown in a retracted configuration.
Figure 19:
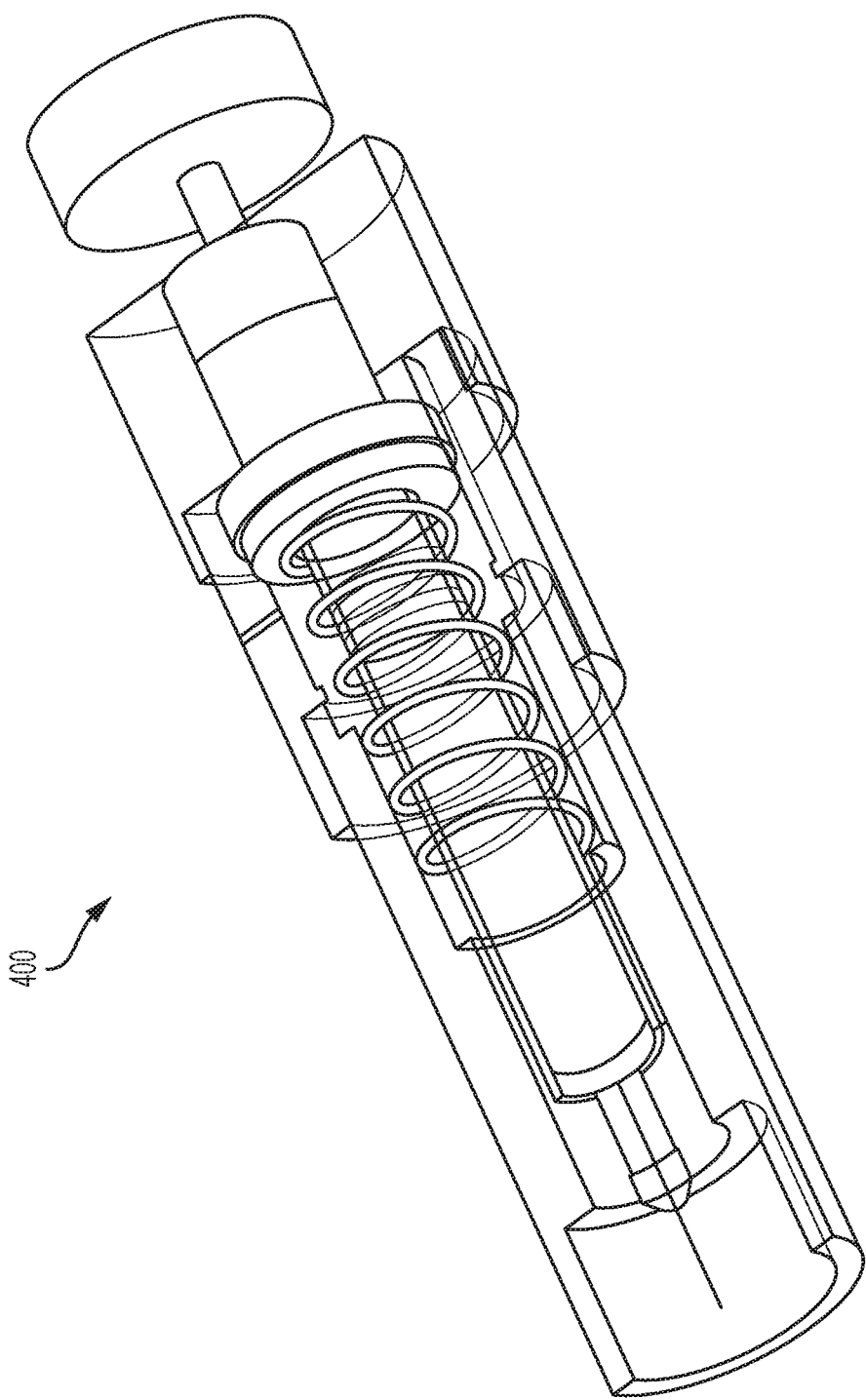
FIG. 19 is a perspective cut-away view of a fourth exemplary delivery device of the present disclosure.

In FIG. 18, device 300 is shown in a retracted configuration. To reach this configuration, the gas from inner chamber 342 of barrel 340 is released from inner chamber 342 and travels through the exposed airway 380 and into outer chamber 346 of barrel 340 defined by outer housing 335. Eventually, the proximal force on head 341 of barrel 340 is sufficient to cause proximal movement of barrel 340 and syringe 310. When the proximal force eventually exceeds the distal force after a certain delay time, barrel 340 moves proximally through outer housing 335. In this manner, barrel 340 serves as a second piston inside outer housing 335. The proximal movement of barrel 340, including the delay time before movement, may be controlled by adjusting the size and shape of barrel 340, the size and shape of first piston 360, and the size of airway 380, for example. Like devices 100 and 200, for example, the surface area of head 341 of barrel 340 may exceed the surface area of head 362 of piston 360 to promote retraction of barrel 340. Due to frictional forces between syringe 310 and plunger 320, the proximal movement of barrel 340 causes proximal movement of syringe 310. At distal end 302 of device 300, needle 314 withdraws from the puncture site and retracts into shield 330. Needle 314 may have the same position in the retracted configuration of FIG. 18 as the loaded configuration of FIG. 13. Body 335 may be captured at the end of the proximal stroke to maintain needle 314 in the retracted configuration.

6. Fourth Embodiment

FIGS. 19-27 show a fourth exemplary delivery device 400 of the present disclosure. The illustrative device 400 is an elongate structure that extends along longitudinal axis L from a first, distal end 402 (illustratively, a lower end) to a second, proximal end 404 (illustratively, an upper end). Advantageously, device 400 may have a compact construction and a relatively short length. Device 400 includes a syringe 410, a plunger 420, a shield 430, a barrel 440, an actuator assembly 450, a first piston 460, an airway 480, and a spring 490. Each component of device 400 is described further below with continued reference to FIGS. 19-27.

The illustrative syringe 410 contains a therapeutic fluid 412, as discussed above. At distal end 402, syringe 410 includes a needle 414 configured to puncture a patient's skin. At its other end, syringe 410 includes a rim 416. In use, syringe 410 is configured for longitudinal movement with first piston 460 relative to shield 430 and barrel 440.

The illustrative plunger 420 is disposed within syringe 410. In use, plunger 420 is configured for longitudinal movement within syringe 410.

The illustrative shield 430 is disposed around syringe 410 and is coupled (e.g., threaded, welded) to barrel 440. It is also within the scope of the present disclosure for shield 430 to be integrally formed with barrel 440.

The illustrative barrel 440 is substantially cylindrical in shape, although this shape may vary. Barrel 440 includes an upper chamber 442 having a relatively large internal diameter and detent 448 configured to interact with first piston 460 surrounding syringe 410 to limit distal movement of first piston 460 and syringe 410.

The illustrative actuator assembly 450 includes a button 451 having a sharp distal tip 452. The illustrative actuator assembly 450 also includes a housing 453 having an interior barrier 454 (e.g., film). In the illustrated embodiment of FIG. 20, housing 453 of actuator assembly 450 is a separate component coupled (e.g., threaded, welded) to barrel 440, but it is also within the scope of the present disclosure for housing 453 of actuator assembly 450 to be integrally formed with barrel 440. In the configuration shown in FIG. 20, interior barrier 454 divides housing 453 into a first actuation chamber 455 that contains a first reagent 456 (e.g., aqueous citric acid) and a second reaction chamber 457 that contains a second reagent 458 (e.g., potassium bicarbonate).

The illustrative first piston 460 surrounds syringe 410 below rim 416. In use, first piston 460 is configured to interact with rim 416 of syringe 410 and a detent 448 of barrel 440.

The illustrative airway 480 connects upper chamber 442 of barrel 440 to the surrounding atmosphere. It is also within the scope of the present disclosure for airway 480 to be an external or internal tube that extends from a portion of upper chamber 442 above first piston 460 to a portion of upper chamber 442 below first piston 460. In use, when airway 480 is open, airway 480 is configured to direct gas from upper chamber 442 of barrel 440 into the atmosphere.

Referring next to FIGS. 20-27, an exemplary method is shown and described for operating device 400.

Figure 20:
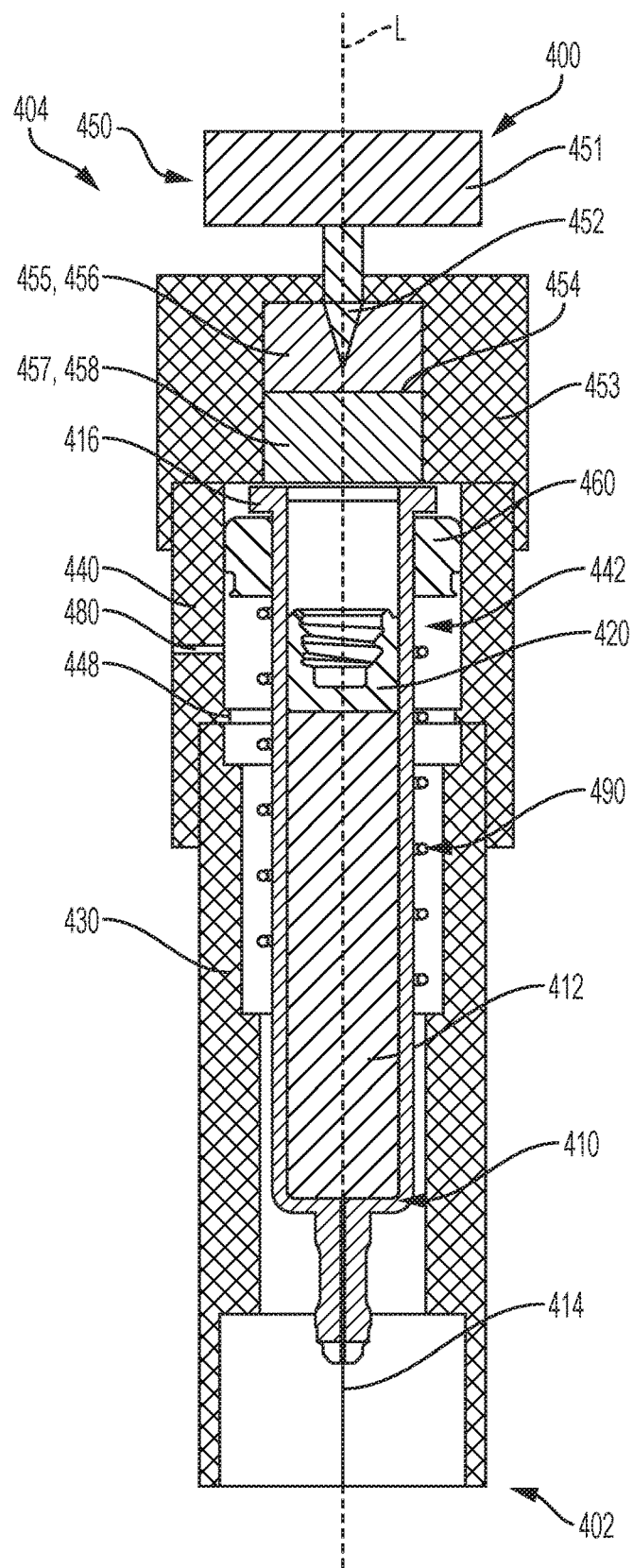
FIG. 20 is a cross-sectional view of the fourth delivery device of FIG. 19, shown in a loaded configuration.

In FIG. 20, device 400 is shown in a loaded configuration. It is within the scope of the present disclosure for device 400 to be locked in this loaded configuration until device 400 is ready for use. At distal end 402 of device 400, syringe 410 and needle 414 are withdrawn into and concealed by shield 430. At proximal end 404 of device 400, interior barrier 454 of actuator assembly 450 separates first reagent 456 (e.g., aqueous citric acid) in first actuation chamber 455 from second reagent 458 (e.g., potassium bicarbonate) in second reaction chamber 457.

Figure 21:
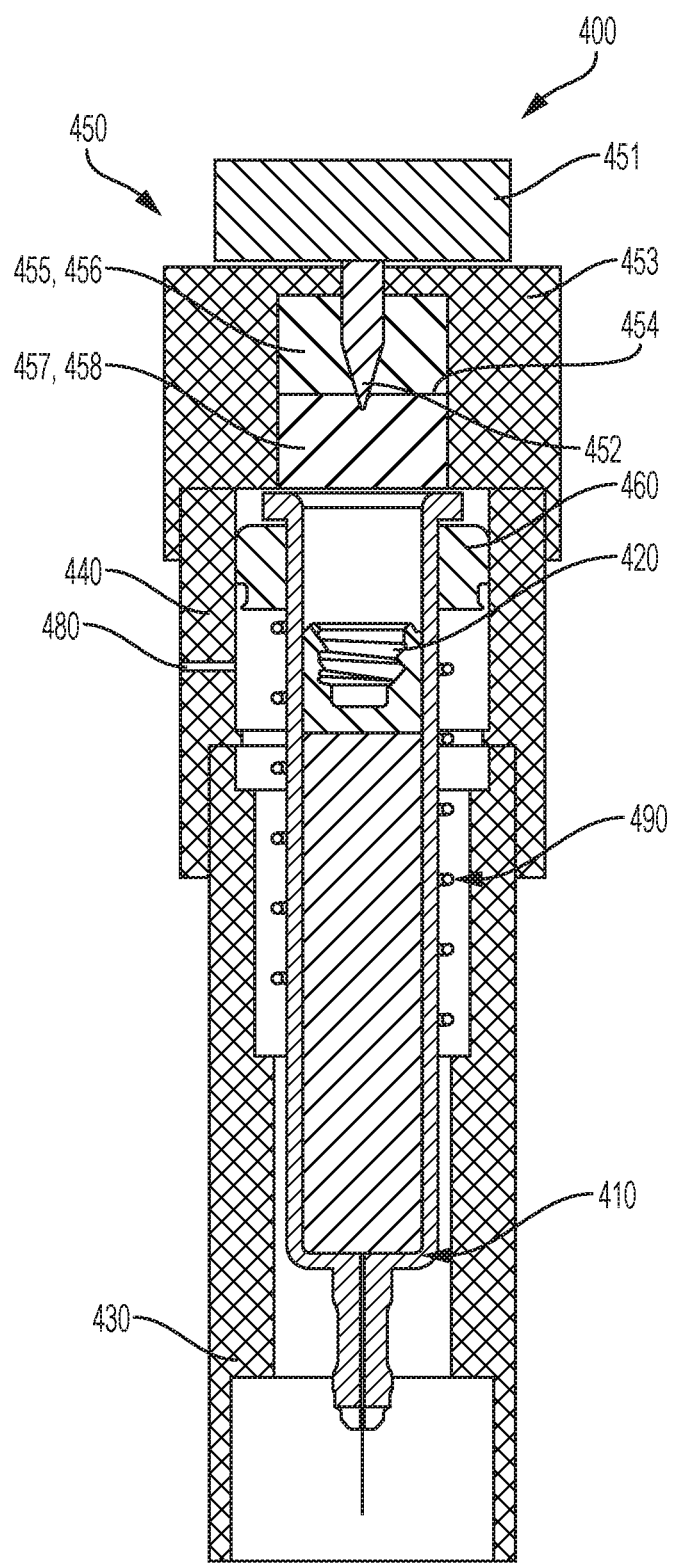
FIG. 21 is another cross-sectional view of the fourth delivery device of FIG. 19, shown in an actuated configuration.

In FIG. 21, device 400 is shown in an actuated configuration. Button 451 of actuator assembly 450 has been pressed to pierce interior barrier 454 with tip 452. As a result, interior barrier 454 between first reaction chamber 455 and second reaction chamber 457 is at least partially removed such that first reagent 456 (e.g., aqueous citric acid) in first actuation chamber 455 is exposed to second reagent 458 (e.g., potassium bicarbonate) in second reaction chamber 457.

Additional details regarding actuator assembly 450 and other suitable actuator assemblies are described in the above-incorporated U.S. Pat. Nos. 9,321,581; 9,795,740; and International Application No. PCT/US2018/017547, as discussed above.

Figure 22:
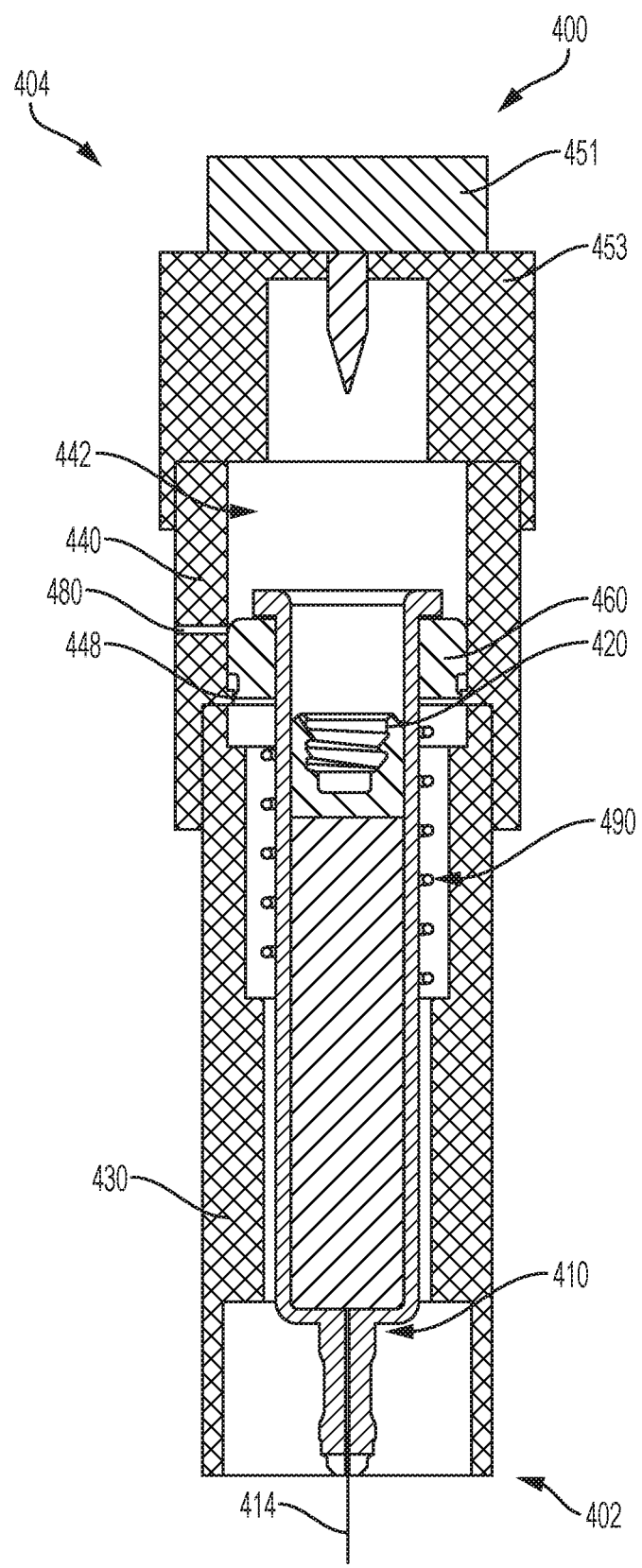
FIG. 22 is another cross-sectional view of the fourth delivery device of FIG. 19, shown in a punctured configuration.

In FIG. 22, device 400 is shown in a punctured configuration. At proximal end 404 of device 400, first and second reagents 456, 458 react and generate gas. The gas pressurizes upper chamber 442 of barrel 440 and applies force to first piston 460 and syringe 410, which causes first piston 460 and syringe 410 to move distally through barrel 440 in turn causing spring 490 to compress. Due to frictional forces between syringe 410 and plunger 420, the initial distal movement of first piston 460 causes distal movement of syringe 410, until first piston 460 abuts detent 448 of barrel 440. At distal end 402 of device 400, needle 414 protrudes from shield 430 to puncture the patient's skin.

Figure 23:
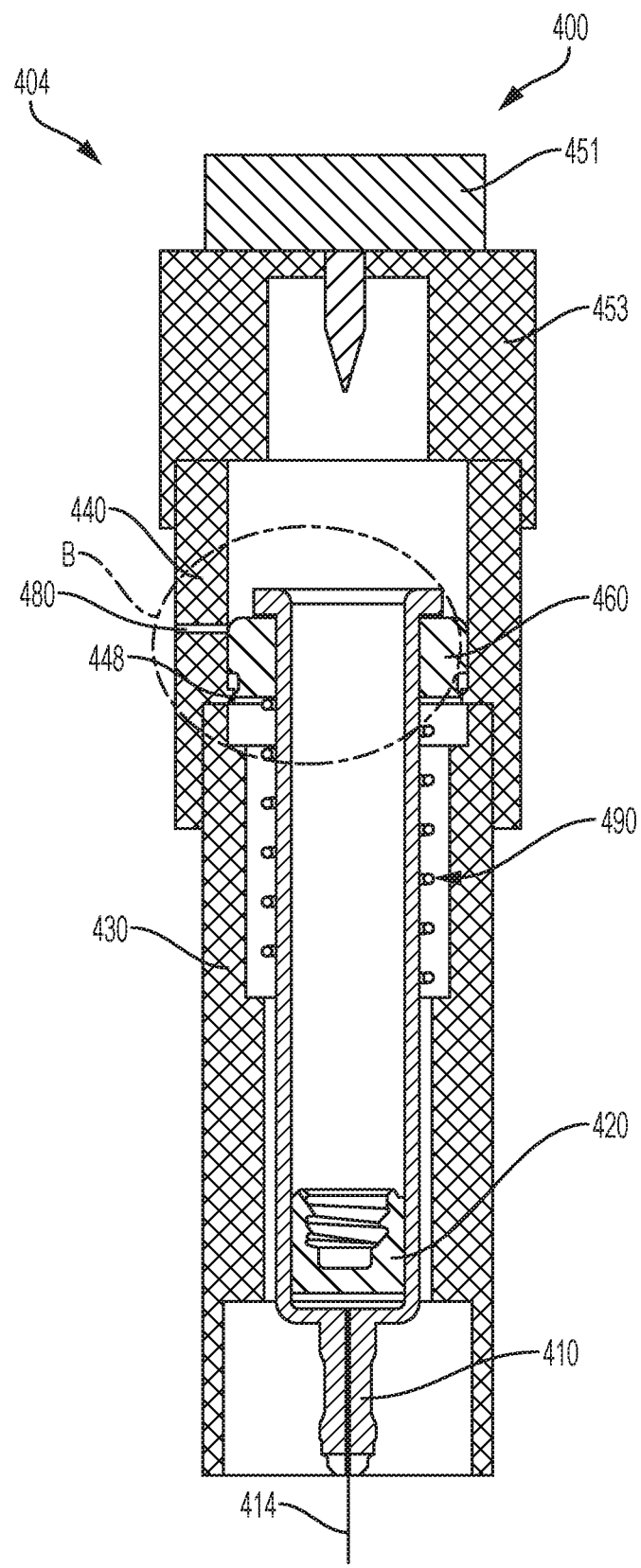
FIG. 23 is another cross-sectional view of the fourth delivery device of FIG. 19, shown in an injected configuration.
Figure 24:
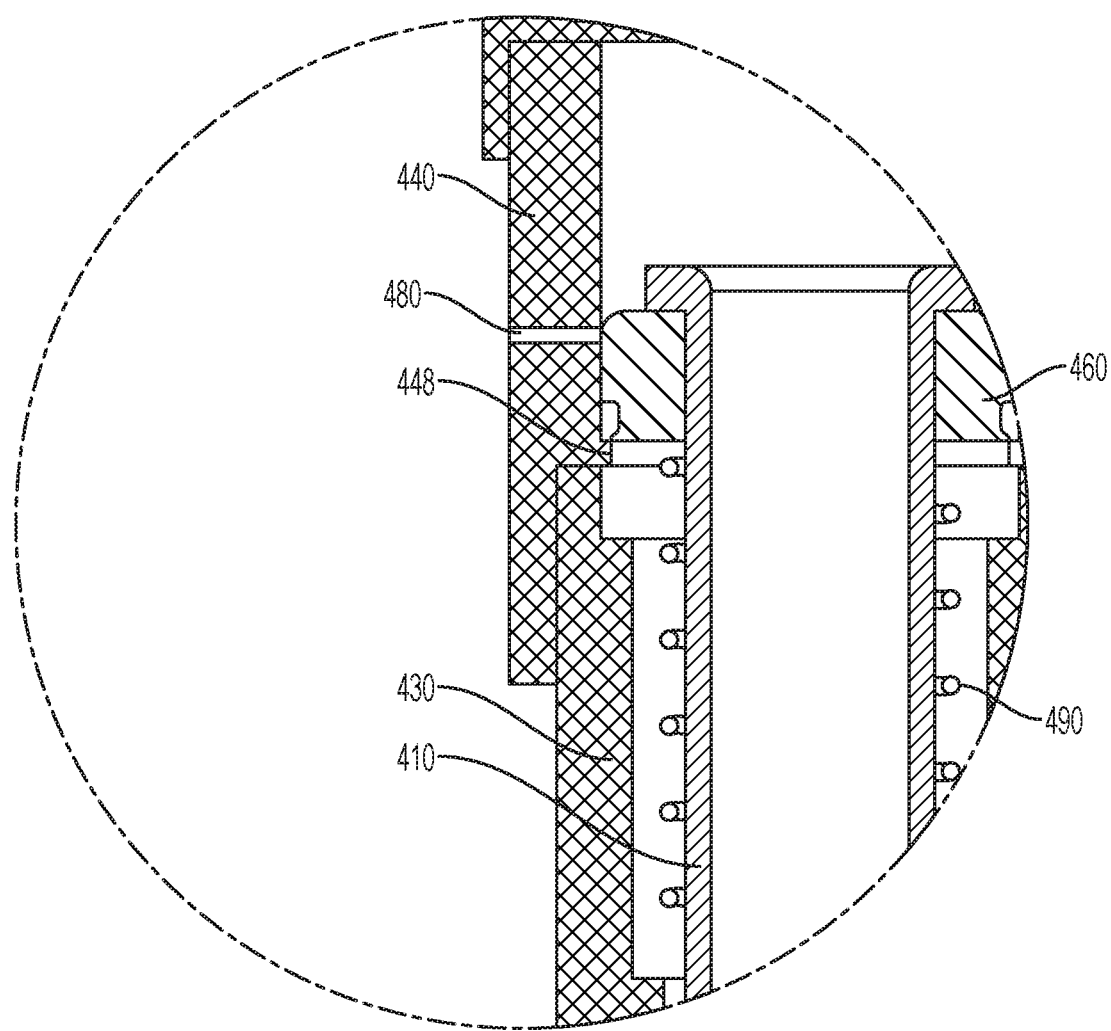
FIG. 24 is a detailed view of section B of the fourth delivery device of FIG. 23.
Figure 25:
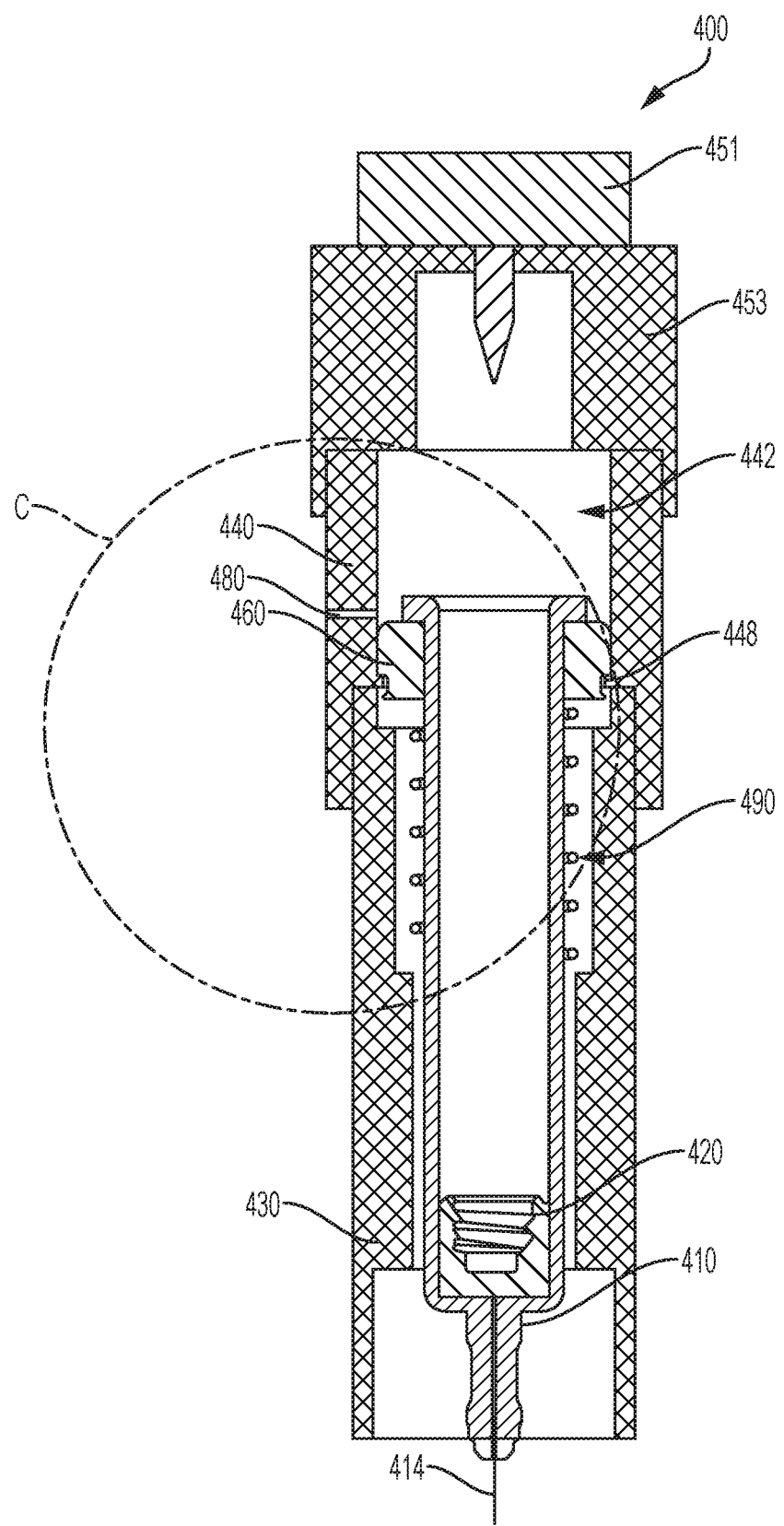
FIG. 25 is another cross-sectional view of the fourth delivery device of FIG. 19 shown in the injected configuration at the end of a full distal stroke.
Figure 26:
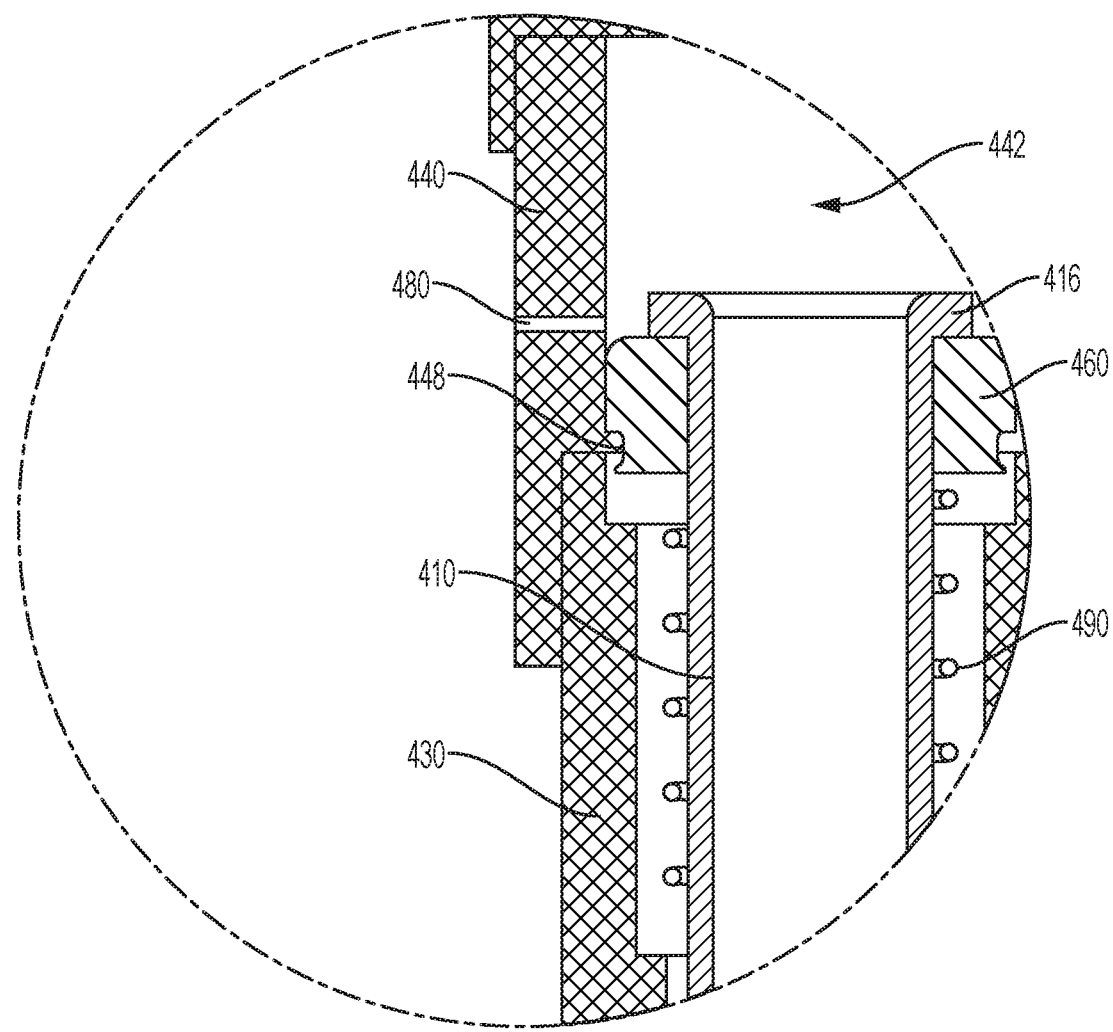
FIG. 26 is a detailed view of section C of the fourth delivery device of FIG. 25.

In FIG. 23, device 400 is shown in an injected configuration. At proximal end 404 of device 400, first and second reagents 456, 458 continue to react and generate gas. With first piston 460 abutting an upper surface of detent 448 of barrel 440, as shown in FIG. 24, the continued pressure increase within upper chamber 442 of barrel 440 overcomes frictional forces between plunger 420 and syringe 410 and causes distal movement of plunger 420 through syringe 410 to deliver therapeutic fluid 412 from syringe 410, through needle 414, and into the puncture site. When plunger 420 reaches the end of its distal stroke, as shown in FIG. 25, pressure within upper chamber 442 becomes sufficient to move first piston 460 down over detent 448, as shown in FIG. 26, and exposes airway 480.

Figure 27:
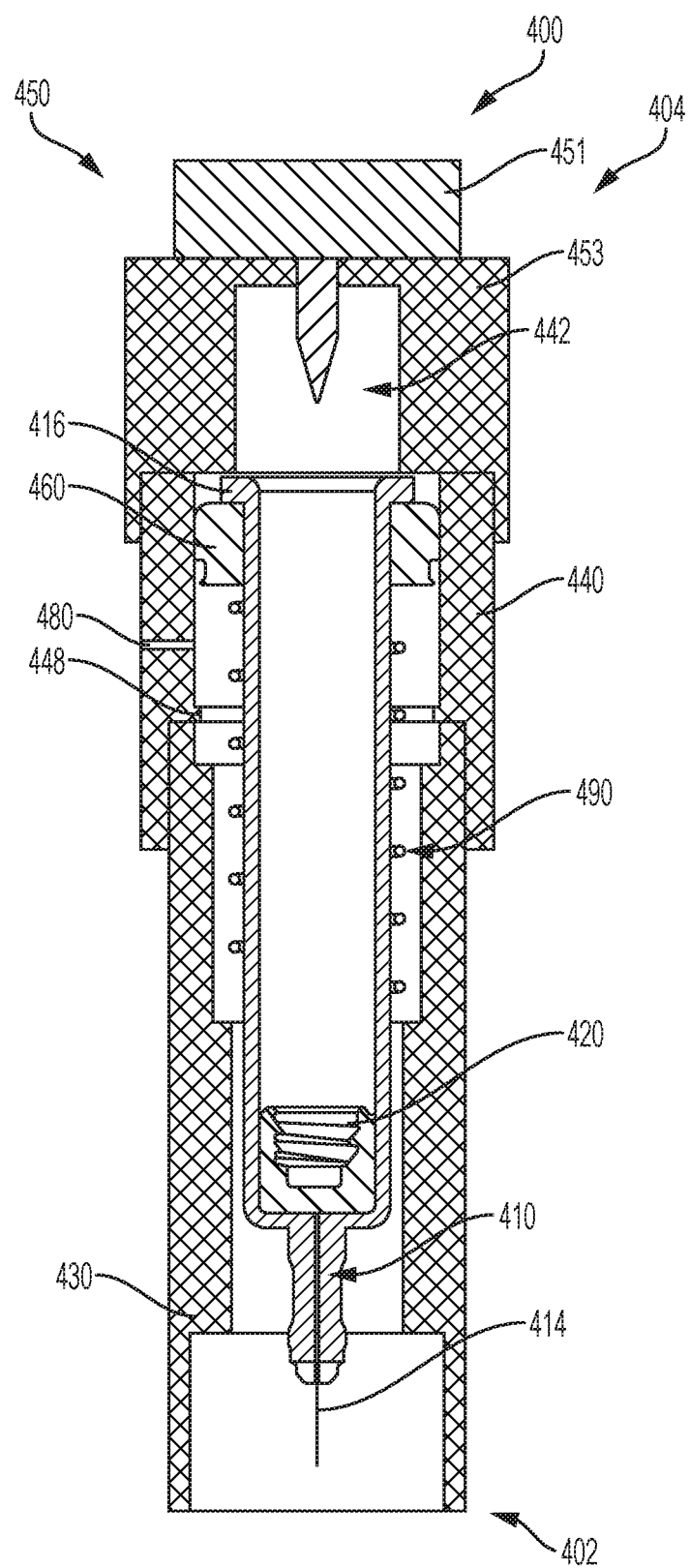
FIG. 27 is another cross-sectional view of the fourth delivery device of FIG. 19, shown in a retracted configuration.

In FIG. 27, device 400 is shown in a retracted configuration. To reach this configuration, the gas from upper chamber 442 of barrel 440 is released from upper chamber 442 and travels through the exposed airway 480 out of barrel 440. Eventually, when the proximal force on first piston 460 from spring 490 exceeds the distal force on first piston 460 from the pressurized gas and the frictional force on first piston 460 from detent 448 after a certain delay time, first piston 460 and syringe 410 move proximally through upper chamber 442 of barrel 440 toward actuator assembly 450. The proximal movement of first piston 460, including the delay time before movement, may be controlled by adjusting the size, shape, and spring constant of spring 490, the size and shape of detent 448, and the size of airway 480, for example. Due to rim 416 of syringe 410 being above first piston 460 within upper chamber 442 of barrel 440, the proximal movement of first piston 460 causes proximal movement of syringe 410. At distal end 402 of device 400, needle 414 withdraws from the puncture site and retracts into shield 430. Needle 414 may have the same position in the retracted configuration of FIG. 27 as in the loaded configuration of FIG. 20. First piston 460 may be captured at the end of the proximal stroke to maintain needle 414 in the retracted configuration.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for delivering a therapeutic fluid by chemical reaction, the device comprising:
   a barrel including a first chamber and a second chamber;
   an actuator assembly coupled to the barrel and including a first reagent and a second reagent;
   a syringe coupled to the barrel, the syringe containing the therapeutic fluid and including a needle; and
   a plunger disposed in the syringe;
   wherein the device includes a first piston and a second piston, the first piston is coupled to the plunger, and the device has:
      an actuated configuration in which the first and second reagents react and generate a gas;
      an injected configuration in which the gas applies a force to the first piston to move the plunger in a first direction to deliver the therapeutic fluid from the syringe; and
      a retracted configuration in which the gas is routed from the first chamber through an airway to the second chamber to apply a force to the second piston to move the needle of the syringe in a second direction opposite the first direction.

2. The device of claim 1, wherein the device has an extended needle configuration following the actuated configuration in which the gas moves the needle of the syringe in the first direction to puncture the skin of a patient.

3. The device of claim 2, further comprising a shield disposed around the syringe, wherein the needle of the syringe extends from the shield in the extended needle configuration and is concealed by the shield in the retracted configuration.

4. The device of claim 1, wherein the device has a loaded configuration in which the first and second reagents are separated from each other.

5. The device of claim 1, wherein the first piston includes a first piston head and the second piston includes a second piston head, the gas acting on the first piston head in the injected configuration and on the second piston head in the retracted configuration, wherein in the injected configuration the movement of the first piston in the first direction exposes the airway following the delivery of the fluid.

6. The device of claim 5, wherein the second piston head has a larger surface area than the first piston head.

7. The device of claim 5, wherein the second piston head is configured to move axially relative to the first piston head.

8. The device of claim 5, where in the second piston head is fixed relative to the first piston head.

9. A device for delivering a therapeutic fluid by chemical reaction, the device comprising:
   a barrel;
   an actuator assembly coupled to the barrel and including a first reagent and a second reagent;
   a syringe coupled to the barrel, the syringe containing the therapeutic fluid and including a needle and a rim;
   a plunger disposed in the syringe; and
   an air chamber in fluid communication with the plunger;
   wherein the device includes a piston surrounding the syringe below the rim, and the device has:
      an actuated configuration in which the first and second reagents react and generate a gas in the air chamber to move the piston and the syringe in a distal direction;
      an injected configuration in which the gas in the air chamber moves the plunger in a first direction toward a distal end of the syringe to deliver the therapeutic fluid from the syringe, wherein when the plunger is at the distal end the piston moves to expose an air passageway; and
      a retracted configuration in which the gas is released from the air chamber through the air passageway to allow movement of the needle of the syringe in a second direction opposite the first direction.

10. The device of claim 9, wherein the air chamber and the air passageway are separated from each other in the injected configuration and in communication with each other in the retracted configuration, and when the plunger is at the distal end the piston moves over a detent to expose the air passageway.

11. The device of claim 9, further comprising:
    a second air chamber in fluid communication with the air passageway and the piston;
    wherein, in the retracted configuration, the gas travels through the air passageway and into the second air chamber to drive the piston in the second direction.

12. The device of claim 9, wherein the air passageway communicates with the surrounding atmosphere.

13. The device of claim 12, further comprising a spring that is compressed in the injected configuration and released in the retracted configuration to move the needle of the syringe in the second direction opposite the first direction.

14. A method for delivering a therapeutic fluid by chemical reaction from a device comprising a barrel having a first chamber and a second chamber, an actuator assembly coupled to the barrel and including a first reagent and a second reagent separated by a barrier, a syringe coupled to the barrel, the syringe containing the therapeutic fluid and including a needle, a plunger disposed in the syringe, a first piston and a second piston, the first piston coupled to the plunger, and a shield coupled to the barrel and surrounding the syringe, the method including:
   actuating the actuator assembly;
   at least partially removing the barrier between the first reagent and the second reagent;
   generating a gas from a reaction of the first reagent and the second reagent;
   pressurizing the first chamber of the barrel via the generated gas;
   displacing the first piston, the syringe, the plunger, and the needle in a first direction via a force created by the generated gas in the first chamber;
   displacing the plunger within the syringe via the force created by the generated gas;
   delivering the therapeutic fluid from the needle;
   releasing the generated gas from the first chamber within the barrel through an air passageway to the second chamber; and
   displacing the needle and the syringe in a second direction after releasing the generated gas from the first chamber via a force created by the generated gas in the second chamber to the second piston in the second direction.

15. The method of claim 14, wherein the needle of the syringe is positioned entirely within the shield prior to the displacement of the syringe, the plunger, and the needle in the first direction via the force created by the generated gas.

16. The method of claim 14 further comprising exposing the needle of the syringe outside of the shield when the syringe, the plunger, and the needle are displaced in the first direction.

17. The method of claim 14, wherein the second direction is opposite the first direction.

18. The method of claim 14, wherein the step of releasing the generated gas from the first chamber includes the generated gas entering the air passageway after the plunger is displaced within the syringe.

19. The method of claim 18, wherein displacement of the syringe and the needle in the second direction occurs after the generated gas enters the air passageway.

* * * * *